US006995244B2

(12) United States Patent
Brooks et al.

(10) Patent No.: US 6,995,244 B2
(45) Date of Patent: Feb. 7, 2006

(54) ANTAGONISTS FOR HUMAN PROLACTIN

(75) Inventors: Charles L. Brooks, Columbus, OH (US); Francis Peterson, Oak Creek, WI (US)

(73) Assignee: The Ohio State University, Columbus, OH (US)

( * ) Notice: Subject to any disclaimer, the term of this patent is extended or adjusted under 35 U.S.C. 154(b) by 0 days.

(21) Appl. No.: 10/735,594

(22) Filed: Dec. 12, 2003

(65) Prior Publication Data

US 2005/0250689 A1 Nov. 10, 2005

Related U.S. Application Data

(60) Provisional application No. 60/433,370, filed on Dec. 13, 2002.

(51) Int. Cl.
*A61K 38/24* (2006.01)

(52) U.S. Cl. .................................................... 530/399

(58) Field of Classification Search ................ 530/399
See application file for complete search history.

(56) References Cited

U.S. PATENT DOCUMENTS 6,429,186 B1 8/2002 Fuh et al.
2001/0036662 A1 11/2001 Walker
2003/0022833 A1 1/2003 Chen et al.
2004/0127407 A1 * 7/2004 Chen .......................... 514/12

OTHER PUBLICATIONS

Kinet, S., Goffin, V., Mainfroid, V., and Marital, J.A. Characterization of Lactogen Receptor-binding Site 1 of Human Prolactin (1996) J. Biol. Chem. 271(24): 14353-14360.*

Goffin, V., Struman, I., Mainfroid, V., Kinet, S., and Martial, J.A. Evidence for a Second Receptor Binding Site on Human Prolactin (1994) J. Biol. Chem. 269(51): 32598-32606.*

Fuh, G., and Wells, J.A. Prolactin Receptor Antagonists That Inhibit the Growth of Breast Cancer Cell Lines (1995) J. Biol. Chem. 270(22): 13133-13137.*

Goffin, V., Shiverick, K.T., Kelly, P.A., and Marital, J.A. Sequence-Function Relationships Within the Expanding Family of Prolactin Growth Hormone, Placental Lactogen, and Related Proteins in Mammals (1996) Endocrine Reviews 17(4): 385-410.*

Kunkel et al., "Rapid and Efficient Site-Specific Mutagenesis without Phenotypic Selection", *Methods in Enzymology*, vol. 154, pp. 367-382.

Duda et al., "Human growth hormone site 2 lactogenic activity requires a distant tyrosine164", *FEBS Letters*, 1999, vol. 449, pp. 120-124.

Kunkel et al., "Efficient Site-Directed Mutagenesis using Uracil-Containing DNA", *Methods in Enzymology*, 1991, vol. 204, pp. 125-139.

Peterson et al., "Identification of a Motif Associated with the Lactogenic Actions of Human Growth Hormone", *The Journal of Biological Chemistry*, 1997, vol. 272, Issue 34, pp. 21444-21448.

Peterson et al., "Expression, Folding, and Characterization of Small Proteins with Increasing Disulfide Complexity by a pT7-7-Derived Phagemid", *Protein Expression and Purification*, 1999, vol. 15, pp. 16-23.

Munson et al., "LIGAND: A Versatile Computerized Approach for Characterization of Ligand-Binding Systems", *Analytical Biochemistry*, 1980, vol. 107, pp. 220-239.

Chantalat et al., "The Crystal Structure of Wild-Type Growth Hormone at 2.5 A Resolution", *Protein and Peptide Letters*, 1995, vol. 2, No. 2, pp. 333-340.

Somers et al., "The X-ray structure of a growth hormone-prolactin receptor complex", *Letters To Nature*, Dec. 1, 1994, vol. 372, pp. 478-481.

Duda et al., "Identification of Residues Outside the Two Binding Sites That Are Critical for Activation of the Lactyogenic Activity of Human Growth Hormone", *The Journal of Biological Chemistry*, 2003, vol. 278, No. 25, pp. 22734-22739.

Keeler et al., "The Teritary Structure and Backbone Dynamics of Human Prolactin", *Journal of Molecular Biology*, 2003, vol. 328, pp. 1105-1121.

Elkins et al., "Ternary complex between placental lactogen and the extracellular domain of the prolactin receptor", *Nature Structural Biology*, vol. 7, No. 9, pp. 808-815.

Matera et al., "Prolactin is an autocrine growth factor for the Hurkat human T-leukemic cell line", *Journal of Neuroimmunology*, 1997, vol. 79, pp. 12-21.

Bernichtein et al., "Development of Pure Prolactin Receptor Antagonists", *The Journal of Biological Chemistry*, 2003, vol. 278, No. 38, pp. 35988-35999.

Bole-Feysot et al., "Prolactin (PRL) and Its Receptor: Actions, Signal Transduction Pathways and Phenotypes Observed in PRL Receptor Knockout Mice", *Endocrine Reviews*, 1998, vol. 19, No. 3, pp. 225-268.

Clevenger et al., "Prolactin receptor signal transuction in cells of the immune system", *Journal of Endocrinology*, 1998, vol. 157, pp. 187-197.

Wells, James A., "Binding in the growth hormone receptor complex", *Proc. Natl. Acad. Sci. USA*, Jan. 1996, vol. 93, pp. 1-6.

Peterson and Brooks, "Different elements of mini-helix I are required for human growth hormone or prolactin action via the prolactin receptor", *Protein Engineering, Design & Selection* (2004), vol. 17, No. 5, pp. 417-424.

Sivaprasad et al., "Mechanism for Ordered Receptor Binding by Human Prolactin", *Biochemistry* (2004) vol. 43, pp. 13755-13765.

* cited by examiner

*Primary Examiner*—Karen Cochrane Carlson
*Assistant Examiner*—Marsha Tsay
(74) *Attorney, Agent, or Firm*—Calfee, Halter & Griswold

(57) ABSTRACT

A modified human prolactin molecule wherein the prolactin molecule comprises at least one mutation in a region selected from i) amino acids 41–57, ii) amino acids 94–110, and iii) amino acids 160–173; and wherein the at least one mutation is selected from deletions, replacements, and insertions. The modified prolactins are prolactin antagonists, and can be used in treating cancer, among other conditions.

3 Claims, 18 Drawing Sheets

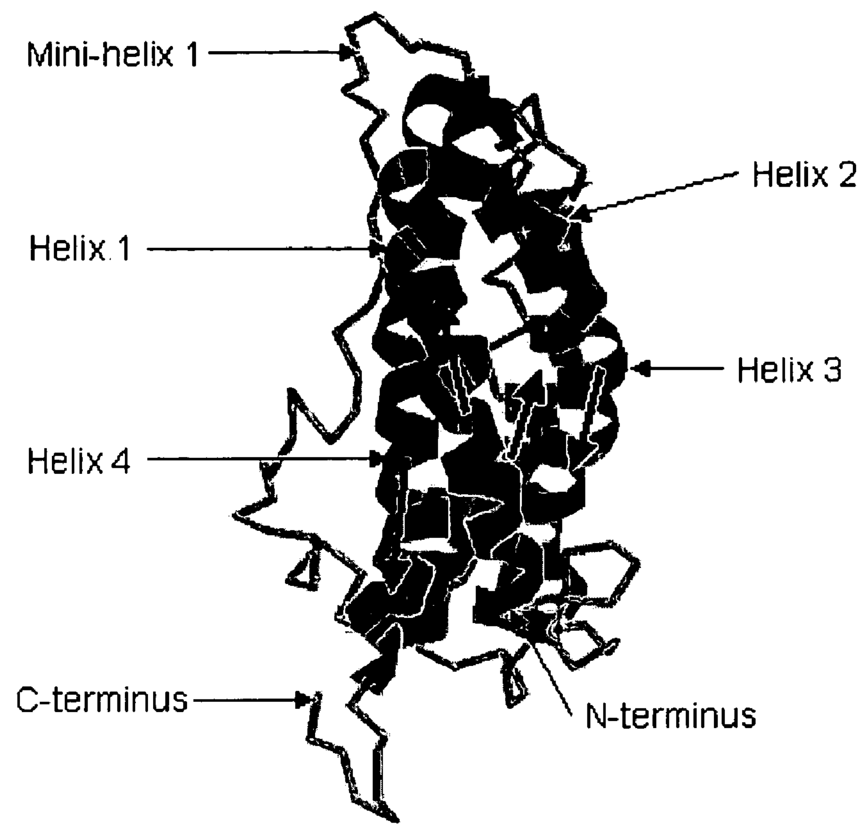
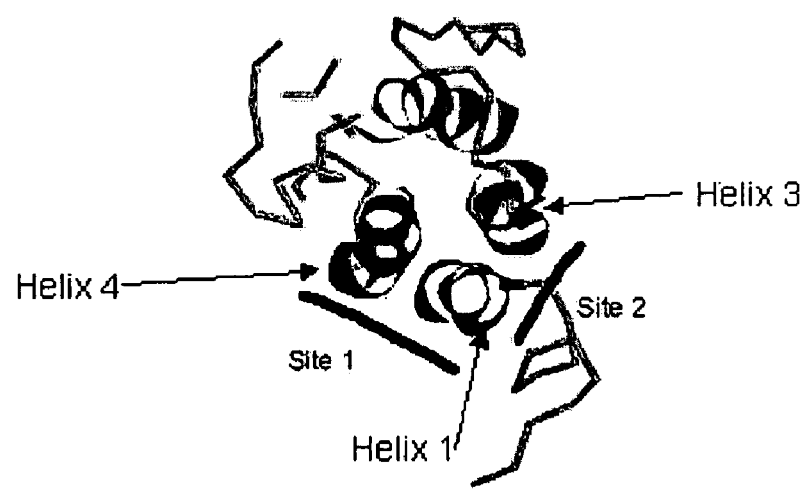
Figure 1

1 gggatcctta ttctatatct cttggtattt agtgtaaaaa ttttaaaatc tttacctagc
61 aatcttgagg aagaaacttg ataactgata atacatgaga ttgttaccta agtgaaatat
121 aatcctatat attcaacaaa ctttagagaa ataagataaa ttttaaagta aatgacttct
181 gtagttttat agatcctcca aaccaatcta gtctcagatc tcaccttcat catttctctc
241 atttcctttt ggcctaatta atcaaaatcc ttcctagaat gttcatttct ggccagtatg
301 tcttcctgaa tatgaataag aaataaaata ccatttgatg tttgaaatta tgggggtaat
361 ctcaatgacg gaaatagatg accaggaaaa gggaaacgaa tgcctgattc attatattca
421 tgaagatatc aaaggtttat aaagccaata tctgggaaag agaaaaccgt gagacttcca
481 gatcttctct ggtgaagtgt gtttcctgca acgatcacga acatgaacat caaaggatcg
541 ccatggaaag ggtccctcct gctgctgctg gtgtcaaacc tgctcctgtg ccagagcgtg
601 gccccttgc ccatctgtcc cggcggggct gcccgatgcc aggtgaccct tcgagacctg
661 tttgaccgcg ccgtcgtcct gtcccactac atccataacc tctcctcaga aatgttcagc
721 gaattcgata aacggtatac ccatggccgg gggttcatta ccaaggccat caacagctgc
781 cacacttctt cccttgccac ccccgaagac aaggagcaag cccaacagat gaatcaaaaa
841 gactttctga gcctgatagt cagcatattg cgatcctgga atgagcctct gtatcatctg
901 gtcacggaag tacgtggtat gcaagaagcc ccggaggcta tcctatccaa agctgtagag
961 attgaggagc aaaccaaacg gcttctagag ggcatggagc tgatagtcag ccaggttcat
1021 cctgaaacca aagaaaatga gatctaccct gtctggtcgg gacttccatc cctgcagatg
1081 gctgatgaag agtctcgcct ttctgcttat tataacctgc tccactgcct acgcagggat
1141 tcacataaaa tcgacaatta tctcaagctc ctgaagtgcc gaatcatcca caacaacaac
1201 tgctaagccc acatccattt catctatttc tgagaaggtc cttaatgatc cgttccattg
1261 caagcttctt ttagttgtat ctcttttgaa tccatgcttg ggtgtaacag gtctcctctt
1321 aaaaaataaa aactgactcc ttagagacat caaaatccaa aaaaaaaaaa aaaaaaaaaa
1381 aaaaaaaa

Figure 3

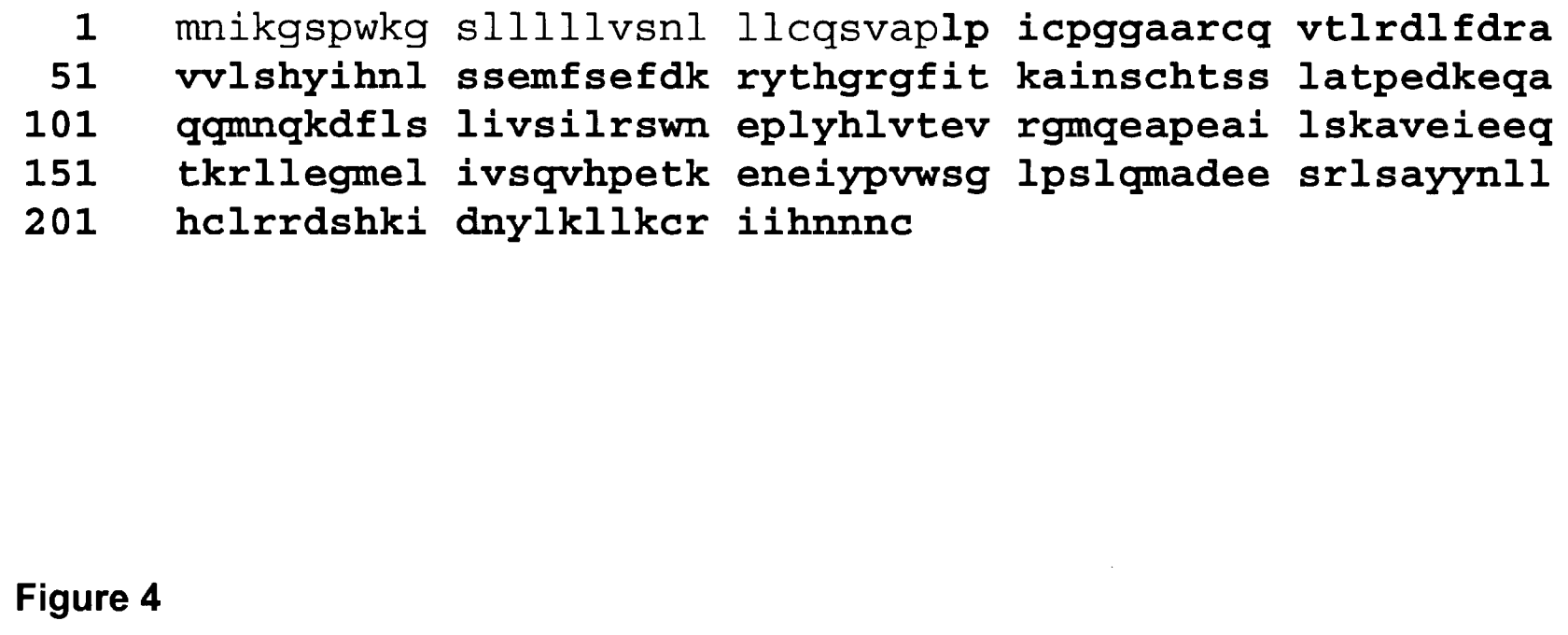

1 mnikgspwkg slllllvsnl llcqsvaplp icpggaarcq vtlrdlfdra
51 vvlshyihnl ssemfsefdk rythgrgfit kainschtss latpedkeqa
101 qqmnqkdfls livsilrswn eplyhlvtev rgmqeapeai lskaveieeq
151 tkrllegmel ivsqvhpetk eneiypvwsg lpslqmadee srlsayynll
201 hclrrdshki dnylkllkcr iihnnnc

Figure 4

MLPICPGGAARCQVTLRDLFDRAVVLSHYIHNLSSE
MFSEFDKRYTHGRGFITKAINSCHTSSLATPEDKE
QAQQMNQKDFLSLIVSILRSWNEPLYHLVTEVRG
MQEAPEAILSKAVEIEEQTKRLLEGMELIVSQVHPE
TKENEIYPVWSGLPSLQMADEESRLSAYYNLLHCL
RRDSHKIDNYLKLLKCRIIHNNNC

Figure 5

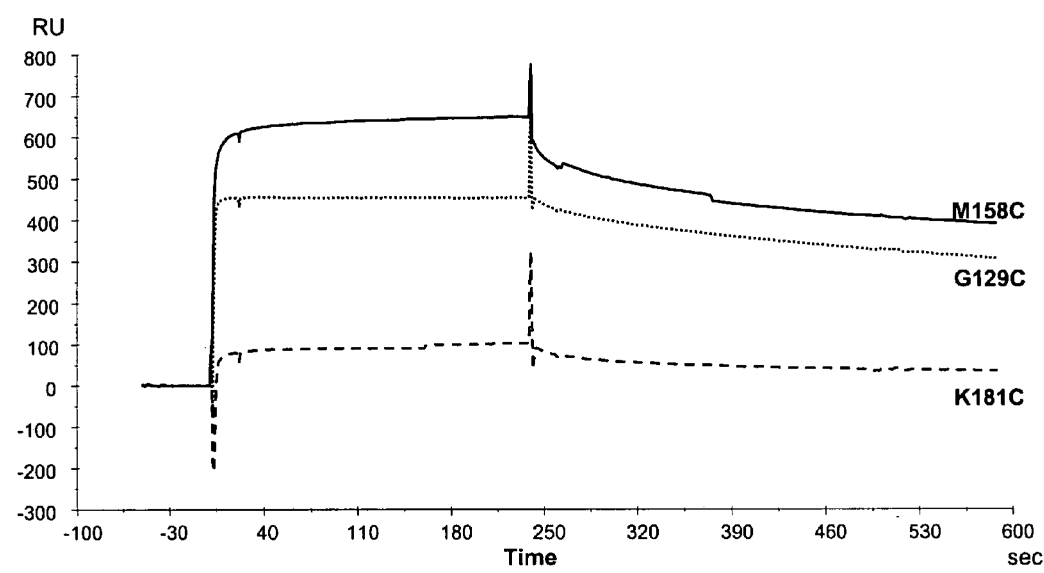
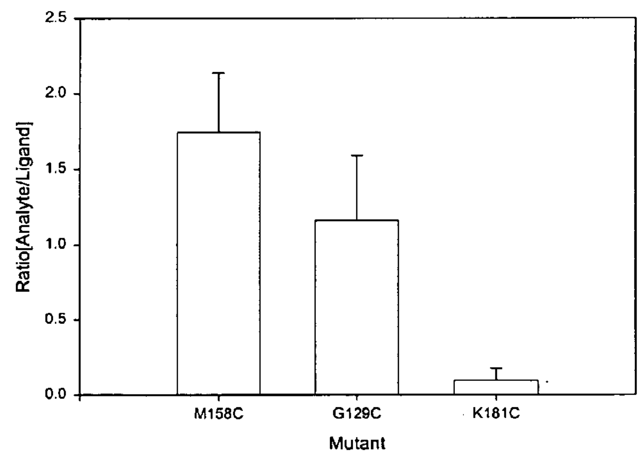
Figure 10

T47D cells treated for 48 hours with 500 nM Δ41-52 human prolactin

T47D cells treated for 48 hours with 0.3 nM wild-type human prolactin

SEQUENCE LISTING

```
<160> NUMBER OF SEQ ID NOS: 4

<210> SEQ ID NO 1
<211> LENGTH: 199
<212> TYPE: PRT
<213> ORGANISM: Homo sapiens
```

<400> SEQUENCE: 1

```
Leu Pro Ile Cys Pro Gly Gly Ala Ala Arg Cys Gln Val Thr Leu Arg
  1               5                  10                  15

Asp Leu Phe Asp Arg Ala Val Val Leu Ser His Tyr Ile His Asn Leu
             20                  25                  30

Ser Ser Glu Met Phe Ser Glu Phe Asp Lys Arg Tyr Thr His Gly Arg
         35                  40                  45

Gly Phe Ile Thr Lys Ala Ile Asn Ser Cys His Thr Ser Ser Leu Ala
     50                  55                  60

Thr Pro Glu Asp Lys Glu Gln Ala Gln Gln Met Asn Gln Lys Asp Phe
 65                  70                  75                  80

Leu Ser Leu Ile Val Ser Ile Leu Arg Ser Trp Asn Glu Pro Leu Tyr
                 85                  90                  95

His Leu Val Thr Glu Val Arg Gly Met Gln Glu Ala Pro Glu Ala Ile
            100                 105                 110

Leu Ser Lys Ala Val Glu Ile Glu Glu Gln Thr Lys Arg Leu Leu Glu
        115                 120                 125

Gly Met Glu Leu Ile Val Ser Gln Val His Pro Glu Thr Lys Glu Asn
    130                 135                 140

Glu Ile Tyr Pro Val Trp Ser Gly Leu Pro Ser Leu Gln Met Ala Asp
145                 150                 155                 160

Glu Glu Ser Arg Leu Ser Ala Tyr Tyr Asn Leu Leu His Cys Leu Arg
                165                 170                 175

Arg Asp Ser His Lys Ile Asp Asn Tyr Leu Lys Leu Leu Lys Cys Arg
            180                 185                 190

Ile Ile His Asn Asn Asn Cys
        195
```

<210> SEQ ID NO 2
<211> LENGTH: 1388
<212> TYPE: DNA
<213> ORGANISM: Homo sapiens

<400> SEQUENCE: 2

```
gggatcctta ttctatatct cttggtattt agtgtaaaaa ttttaaaatc tttacctagc     60

aatcttgagg aagaaacttg ataactgata atacatgaga ttgttaccta agtgaaatat    120

aatcctatat attcaacaaa ctttagagaa ataagataaa ttttaaagta aatgacttct    180

gtagttttat agatcctcca aaccaatcta gtctcagatc tcaccttcat catttctctc    240

atttcctttt ggcctaatta atcaaaatcc ttcctagaat gttcatttct ggccagtatg    300

tcttcctgaa tatgaataag aaataaaata ccatttgatg tttgaaatta tgggggtaat    360

ctcaatgacg gaaatagatg accaggaaaa gggaaacgaa tgcctgattc attatattca    420

tgaagatatc aaaggtttat aaagccaata tctgggaaag agaaaaccgt gagacttcca    480

gatcttctct ggtgaagtgt gtttcctgca acgatcacga acatgaacat caaaggatcg    540

ccatggaaag ggtccctcct gctgctgctg gtgtcaaacc tgctcctgtg ccagagcgtg    600

gccccccttgc ccatctgtcc cggcggggct gcccgatgcc aggtgaccct tcgagacctg    660

tttgaccgcg ccgtcgtcct gtcccactac atccataacc tctcctcaga aatgttcagc    720

gaattcgata aacggtatac ccatggccgg gggttcatta ccaaggccat caacagctgc    780

cacacttctt cccttgccac ccccgaagac aaggagcaag cccaacagat gaatcaaaaa    840

gactttctga gcctgatagt cagcatattg cgatcctgga atgagcctct gtatcatctg    900
```

```
gtcacggaag tacgtggtat gcaagaagcc ccggaggcta tcctatccaa agctgtagag    960

attgaggagc aaaccaaacg gcttctagag ggcatggagc tgatagtcag ccaggttcat   1020

cctgaaacca aagaaaatga gatctaccct gtctggtcgg gacttccatc cctgcagatg   1080

gctgatgaag agtctcgcct ttctgcttat tataacctgc tccactgcct acgcagggat   1140

tcacataaaa tcgacaatta tctcaagctc ctgaagtgcc gaatcatcca caacaacaac   1200

tgctaagccc acatccattt catctatttc tgagaaggtc cttaatgatc cgttccattg   1260

caagcttctt ttagttgtat ctcttttgaa tccatgcttg ggtgtaacag gtctcctctt   1320

aaaaaataaa aactgactcc ttagagacat caaaatccaa aaaaaaaaaa aaaaaaaaaa   1380

aaaaaaaa                                                            1388
```

<210> SEQ ID NO 3
<211> LENGTH: 227
<212> TYPE: PRT
<213> ORGANISM: Homo sapiens

<400> SEQUENCE: 3

```
Met Asn Ile Lys Gly Ser Pro Trp Lys Gly Ser Leu Leu Leu Leu Leu
  1               5                  10                  15

Val Ser Asn Leu Leu Leu Cys Gln Ser Val Ala Pro Leu Pro Ile Cys
             20                  25                  30

Pro Gly Gly Ala Ala Arg Cys Gln Val Thr Leu Arg Asp Leu Phe Asp
         35                  40                  45

Arg Ala Val Val Leu Ser His Tyr Ile His Asn Leu Ser Ser Glu Met
     50                  55                  60

Phe Ser Glu Phe Asp Lys Arg Tyr Thr His Gly Arg Gly Phe Ile Thr
 65                  70                  75                  80

Lys Ala Ile Asn Ser Cys His Thr Ser Ser Leu Ala Thr Pro Glu Asp
                 85                  90                  95

Lys Glu Gln Ala Gln Gln Met Asn Gln Lys Asp Phe Leu Ser Leu Ile
            100                 105                 110

Val Ser Ile Leu Arg Ser Trp Asn Glu Pro Leu Tyr His Leu Val Thr
        115                 120                 125

Glu Val Arg Gly Met Gln Glu Ala Pro Glu Ala Ile Leu Ser Lys Ala
    130                 135                 140

Val Glu Ile Glu Glu Gln Thr Lys Arg Leu Leu Glu Gly Met Glu Leu
145                 150                 155                 160

Ile Val Ser Gln Val His Pro Glu Thr Lys Glu Asn Glu Ile Tyr Pro
                165                 170                 175

Val Trp Ser Gly Leu Pro Ser Leu Gln Met Ala Asp Glu Glu Ser Arg
            180                 185                 190

Leu Ser Ala Tyr Tyr Asn Leu Leu His Cys Leu Arg Arg Asp Ser His
        195                 200                 205

Lys Ile Asp Asn Tyr Leu Lys Leu Leu Lys Cys Arg Ile Ile His Asn
    210                 215                 220

Asn Asn Cys
225
```

<210> SEQ ID NO 4
<211> LENGTH: 200
<212> TYPE: PRT
<213> ORGANISM: Homo sapiens

<400> SEQUENCE: 4

-continued

```
Met Leu Pro Ile Cys Pro Gly Gly Ala Ala Arg Cys Gln Val Thr Leu
  1               5                  10                  15

Arg Asp Leu Phe Asp Arg Ala Val Val Leu Ser His Tyr Ile His Asn
             20                  25                  30

Leu Ser Ser Glu Met Phe Ser Glu Phe Asp Lys Arg Tyr Thr His Gly
         35                  40                  45

Arg Gly Phe Ile Thr Lys Ala Ile Asn Ser Cys His Thr Ser Ser Leu
     50                  55                  60

Ala Thr Pro Glu Asp Lys Glu Gln Ala Gln Gln Met Asn Gln Lys Asp
 65                  70                  75                  80

Phe Leu Ser Leu Ile Val Ser Ile Leu Arg Ser Trp Asn Glu Pro Leu
                 85                  90                  95

Tyr His Leu Val Thr Glu Val Arg Gly Met Gln Glu Ala Pro Glu Ala
            100                 105                 110

Ile Leu Ser Lys Ala Val Glu Ile Glu Glu Gln Thr Lys Arg Leu Leu
        115                 120                 125

Glu Gly Met Glu Leu Ile Val Ser Gln Val His Pro Glu Thr Lys Glu
    130                 135                 140

Asn Glu Ile Tyr Pro Val Trp Ser Gly Leu Pro Ser Leu Gln Met Ala
145                 150                 155                 160

Asp Glu Glu Ser Arg Leu Ser Ala Tyr Tyr Asn Leu Leu His Cys Leu
                165                 170                 175

Arg Arg Asp Ser His Lys Ile Asp Asn Tyr Leu Lys Leu Leu Lys Cys
            180                 185                 190

Arg Ile Ile His Asn Asn Asn Cys
        195                 200
```

ANTAGONISTS FOR HUMAN PROLACTIN

DESCRIPTION OF THE INVENTION

This application claims benefit of the filing date of U.S. Provisional Application No. 60/433,370, filed Dec. 13, 2002, the entire disclosure of which is incorporated herein by reference.

ANTAGONISTS FOR HUMAN PROLACTIN

This invention was supported, at least in part, by Grant RO1 DK56117 from the National Institutes of Health. The U.S. government has certain rights in the invention.

FIELD OF THE INVENTION

This invention relates to antagonists for prolactin, including human prolactin.

BACKGROUND OF THE INVENTION

Agonists and Receptors

Cells receive and respond to signals in their environment. Such signals are commonly transmitted to cells by signaling molecules, such molecules also commonly being produced by cells. One type of signaling molecule interacts with, or binds to, cellular receptors. When a signaling molecule binds to a receptor, processes in the target cell that lead to a biological response are initiated. Such processes normally constitute intracellular reactions of various signal transduction pathways. The endpoints of such pathways are changes in a variety of cellular behaviors or responses, including metabolism, differentiation, proliferation, cell death and others. Molecules that interact with receptors are commonly referred to as ligands. Ligands that initiate or affect such cellular behaviors through interaction with receptors are called agonists.

There are many different types of signaling molecules that have agonist activity, examples of which include hormones, growth factors, cytokines, chemokines, neurotransmitters, and the like. Other signaling molecules include steroids, retinoids, thyroxins, prostaglandins, leukotrienes, and others. Substances such as toxins, synthetic molecules and certain drugs can also exert their effects through interaction with receptors. The cellular receptors with which these ligands interact can be intracellular or extracellular. Normally, there is some specificity in interaction of a ligand with a receptor.

Ligands can interact with receptors in a variety of mechanisms. For example, the stoichiometry of the interaction can be one ligand interacting with one receptor. Alternatively, receptors may be able simultaneously to interact with more than one ligand. Ligands may be able to interact with more than one receptor during a binding event.

Prolactin is an example of a ligand that can interact with more than one receptor during a single interaction. Prolactin is an approximately 23,000 Dalton protein that may be found in glycosylated forms. Prolactin is a cytokine in the same family as growth hormone.

Prolactin's tertiary structure has been determined by nuclear magnetic resonance and is an up-up-down-down four-helix bundle topology (FIG. 1). This general structure is similar to those observed for other members of this protein family, including growth hormone and placental lactogen. This topology has also been described as a four-helix bundle scaffold or as a bundle of four alpha helices.

Prolactin has two receptor-binding sites or surfaces. Site 1 is composed of portions of helices 1 and 4. Site 2 is located around the cleft defined by helices 1 and 3. The amino acids that lay within these surfaces form two distinct atomic topologies that bind the prolactin receptors.

The biological responses initiated by prolactin are mediated by its interaction with the prolactin receptor. Prolactin receptor is a Type I cytokine receptor, with a cytoplasmic domain of variable length, a single transmembrane domain and an extracellular domain that interacts with prolactin. The prolactin receptor also bears a high degree of homology to the growth hormone receptor. In fact, primate growth hormones and placental lactogens can bind to and activate the prolactin receptor. In contrast, however, prolactin does not bind to the growth hormone receptor.

Current insights into the molecular mechanisms by which prolactin binds to and activates its receptor are based, at least in part, on the more extensive studies of the interactions of growth hormone with its somatotrophic receptor. Published studies demonstrate that growth hormone activates the growth hormone receptor through a sequential receptor dimerization mechanism (i.e., form ternary complexes or also called ligand-induced receptor oligomerization). In this mechanism, site 1 on the hormone first binds to one molecule of receptor and then site 2 on the hormone binds to a second molecule of receptor.

Supportive evidence for the two-site binding includes the following: (i) Bivalent anti-growth hormone receptor antibodies can activate the receptor, while monovalent Fab antibody fragments cannot. (ii) Crystal structures of growth hormone bound to the extracellular domains of growth hormone receptor or prolactin receptor demonstrate the interaction of two receptor monomers with a single growth hormone molecule through non-symmetrical sites on growth hormone. (iii) In vivo growth hormone display self-antagonism in response to increasing concentrations of growth hormone. The growth responses to low concentrations of growth hormone increase with dose, but high concentrations of growth hormone are inhibitory. A smaller amount of information is available for the interaction of prolactin and the prolactin receptor, but these data also are consistent with sequential receptor dimerization mechanism. As with growth hormone divalent antibodies activate the prolactin receptor while monovalent antibodies do not. Prolactin also antagonizes its activity at high concentrations.

It is thought that prolactin-induced dimerization of prolactin receptor stimulates the JAK-STAT kinase signal transduction pathway to activate gene expression. The cytoplasmic tail of the prolactin receptor does not possess kinase activity. However, ligand-induced dimerization of prolactin receptor leads to the association of the JAK2 kinase with the cytoplasmic portion of the prolactin receptor and results in phosphorylation of both the receptor and JAK2. Phosphorylation of the receptor then leads to association of the transcription factors STAT 1, 3, 5a and 5b with the receptor, via their SH2 domains. The latter association then leads to the phosphorylation of the STAT proteins by the JAK2 kinase. This phosphorylation event is required for subsequent dimerization of the STAT transcription factors, transport to the nucleus and transcriptional activation. STAT5a and STAT5b have been shown to be crucial for the development of the mammary gland. Gene knockouts of these transcription factors mimic many of the features of prolactin receptor knockouts. In particular, STAT5b phosphorylation seems to correlate most closely with proliferative effects in cells.

In addition to the scheme described above, several reports have demonstrated that prolactin can activate elements of the mitogen-activated protein kinase (MAPK) pathway, including the src, the src homology, flyn, Raf-1, and MAP kinases. It is becoming clear that considerable crosstalk exists between the JAK-STAT and MAPK signaling pathways. Some evidence suggests that the STAT proteins can be phosphorylated and activated by both pathways, although the mechanism of activation may be distinct in each case. Nevertheless, phosphorylation of the STAT proteins appears to be an intercellular surrogate marker for the biological effects of prolactin.

The pituitary, placenta, and other tissues of mammals produce prolactin. Prolactin interacts with prolactin receptors, which exist in a variety of tissues including the breast, liver, prostate, kidney, and cells of the immune system. A widely studied biological response action of prolactin is in the development and lactation of the epithelial cells of the breast (mammary tissue). During lactation, lactating epithelial cells of the breast are dependent on prolactin. Prolactin also affects growth, development, and/or survival of tumors of the breast or mammary gland.

Human prolactin is increasingly associated with the development and growth of human breast tumors. Most breast tumors develop from the mammary epithelial cells that produce milk. These tumor cells possess prolactin receptors and produce prolactin. Therefore, it appears that these tumors have acquired an autocrine system: they make their own prolactin and release it into the extracellular space where it binds prolactin receptors of the tumor.

Other tumors appear to be prolactin-dependent or at least prolactin-responsive. For example, prolactin has been implicated in normal prostate development and prostatic hyperplasia and hypertrophy.

Breast cancer and prostate cancer are the second leading causes of cancer-related deaths among women and men, respectively. Together, these two tumor types were responsible for more than 360,000 new cases and 73,000 deaths in the United States during the year 2000. Few therapeutic compounds increase long-term survival or reduce morbidity. For breast cancer, surgery and/or radiotherapy are the mainstays of treatment of localized disease, with cyclophosphamide, doxorubicin, 5-fluorouracil, and paclitaxel commonly used separately or in combination chemotherapeutic regimens. In addition to these now common therapeutic strategies, beneficial effects have been observed with the anti-estrogens and tamoxifen (a partial agonist/partial antagonist of the estrogen receptor), but such responses occur only in patients whose tumors express sufficient concentrations of estrogen receptors.

The situation for prostate cancer is even worse. Prostatectomy and/or radiotherapy are most commonly used to control local disease. However, metastatic disease has proven refractory to nearly all chemotherapeutic regimens tested. The only consistently successful chemotherapeutic approach identified is the complete inhibition of androgen action, which may require both the ablation of testicular androgen synthesis and the administration of anti-androgens to block the effects of androgens secreted by the adrenal glands.

Antagonists

When acting as an agonist, ligand binding to its receptor produces a biological response as described above. Molecules exist that interfere with the ability of ligands to produce their biological responses. Such molecules are called antagonists. Antagonists are substances that suppress, inhibit, or interfere with the biological activity of a native ligand (e.g., a signaling molecule). Antagonists can function in a variety of ways. One way in which antagonists can function is by binding or interacting with a receptor at the same site on the receptor to which an agonist binds. In this case, binding of the antagonist to the receptor inhibits the ability of the agonist to bind to the receptor. Functioning of an antagonist in this way is called competitive antagonism. Another way in which antagonists can function is by binding or interacting with a receptor at a different site on the receptor to which the agonist binds. In this case, binding of the antagonist to the receptor can prevent agonist binding or, if the agonist does bind, transmission of its signal to the signal transduction pathway is inhibited. Functioning of an antagonist in this way is called noncompetitive or uncompetitive antagonism.

Investigators have realized the therapeutic potential of antagonists in certain circumstances. For example, an effective prolactin antagonist would block or inhibit the ability of the body's own prolactin to cause a biological response. Such prolactin antagonists can be used as prophylactic or therapeutic agents for breast cancer, prostate cancer, other prolactin dependent tumors, or can be given to females after the birth of a child for the purpose of reducing or suppressing lactation.

Prolactin antagonists, specifically prolactin variants that have antagonist activity, have been described in the prior art. In these compounds prolactin has been modified by replacing an amino acid within one of the two receptor-binding surfaces of human prolactin (i.e., within site 1 or site 2) with an amino acid that blocks receptor binding (e.g., replacement of a small amino acid with a bulky amino acid) through that site on the ligand. Alternatively, prolactin has been modified by making mutations within amino acids that form the "scaffolding" that holds the global structure of the protein together—such mutations also disrupt the structures of site 1 and/or site 2. In one type of prolactin antagonist, the structure of the site 2 receptor-binding surface is affected to physically block the binding of prolactin to the prolactin receptor at site 2. The logic approach is that by presenting prolactin antagonists to tumor cells that bind but cannot dimerize receptors, prolactin receptors would be bound but not activated. With sufficient receptor binding by antagonists, insufficient receptors would be available for the endogenous agonist to initiate a biological response.

This approach has been marginally successful, producing an antagonist that retains approximately 1% agonist activity. See U.S. Pat. No. 6,429,186, to Fuh et al. This approach produces a less than desirable therapeutic agent, however, because treatment with antagonist concentrations sufficient to interfere with the autocrine prolactin (i.e., high concentrations), produce significant agonist activity. For example, if an effective pharmacological concentration of an antagonist requires a 100-fold excess concentration of antagonist over the endogenous agonist, then retention of 1% agonist activity in the drug will defeat its purpose because the drug's agonist actions will be significant at the required concentrations.

Another approach to creating prolactin antagonists is described in U.S. Patent Application Publication No. 2001/0036662 to Walker. This approach also involves mutation of amino acids believed to be directly involved in binding. However, like the Fuh approach (U.S. Pat. No. 6,429,186), this approach yields a product that exhibits agonist activity—in this case, about 10%. As noted above, this high level of agonist activity is unacceptable.

Therefore, there is a need for improved antagonists, in particular, better prolactin antagonists that efficiently block the activity of prolactin without providing undesirable agonist activity.

SUMMARY OF THE INVENTION

We have discovered the mechanism by which prolactin, and other hormones of its type (i.e. growth hormone or placental lactogen), binds to its cognate receptor. In its unbound state, site 1 but not site 2 of prolactin is available for binding to prolactin receptor. Binding of prolactin to the prolactin receptor through site 1 causes a conformational change in prolactin (i.e., a change in prolactin's tertiary structure) such that site 2 becomes available for binding to the receptor (i.e., an induced-fit mechanism). We have found amino acid regions of prolactin, outside of site 1 and site 2, that are responsible for site 2 becoming available for binding to the prolactin receptor after site 1 has already bound. We have also identified replacements or deletions within these amino acid regions of prolactin that result in prolactin molecules that bind prolactin receptor through site 1, but are unable to undergo the conformational change that is required for site 2 to become available and/or bind to prolactin receptor.

Using this discovery, we have identified mutants, or variants, of prolactin that have prolactin antagonist activity in that they efficiently inhibit the ability of prolactin to transmit a signal that results in a biological response. We have found that these prolactin variants possess very little or no agonist activity. The prolactin variants are mammalian prolactin proteins, including human prolactin proteins that contain specific alterations or mutations such that the variant prolactin proteins are efficient antagonists of prolactin in humans or other mammals.

Such prolactin variants that have antagonist activity are useful for treatment of conditions where it is desired to inhibit or decrease the activity of endogenous prolactins. Such variants are used therapeutically to treat such conditions or prophylactically to prevent the onset of such conditions. Such variants are useful to treat tumors or cancers in a patient where growth, survival, or metastasis is dependent on or responsive to prolactin. One type of cancer for which the prolactin variants are useful is breast cancer. Another type of cancer for which the prolactin variants are useful is prostate cancer. Such prolactin variants can also be administered to females after the birth of a child for the purpose of suppressing lactation.

With respect to human prolactin, the mutations that result in producing variants with effective antagonist activity can be made in regions of the prolactin molecule that play a role in the conformational change prolactin undergoes to make site 2 of the molecule available for binding with prolactin receptor. We have found three such regions.

With respect to human prolactin, mutations can be made to polynucleotides of the DNA that encode the following three regions of the protein to obtain variants with antagonist activity. The three regions are: i) mini-helix 1, encompassing amino acid residues approximately 41–57, ii) helix 4, encompassing amino acid residues approximately 160–173, and iii) the C-terminal portion of helix 2 distal to proline 94, encompassing amino acids approximately 94–110. The numbering of the amino acids referred to above is as shown in FIG. 5 and as explained in the legend for FIG. 5.

In some embodiments, the mutations are not in regions of the molecule that comprises site 1 or site 2 for binding of prolactin to receptor. In these embodiments, the mutations that produce the antagonists of the present invention are in amino acids relied on for the site 1 binding-induced conformational change of the molecule. Such mutations can be to hydrophobic residues that pack within the interior of the protein, and function to propagate the conformation change induced by receptor binding at site 1, and are within one or more of the three regions described above.

The amino acids that constitute the three regions described above, responsible for propagating a site 1 receptor-binding induced conformation change in human prolactin, are largely composed of hydrophobic residues located on the interior of the protein. These three regions contain amino acids that form a hydrophobic core largely within the interior of the protein. The 3-dimensional packing of these amino acid residues is believed to be important for the overall structure and function of the protein. Therefore, deletion (removal of amino acids) or substitution (replacement of one amino acid with another) of these hydrophobic residues disrupts the chemical and mechanical interactions within this region of the protein's interior. Insertion of amino acids into one or more of the three regions responsible for conformation change is also contemplated.

Therefore, in one embodiment, one or more deletion mutations where nucleic acids that encode the above-identified amino acids are removed from the DNA sequence of wild-type prolactin. Deleting amino acids gives especially good results when they minimally corrupt the overall structure of the protein and allow a strong or increased affinity for prolactin receptor at site 1. In one instance, we have made an excellent prolactin antagonist with a deletion of amino acids 41 through 52 of the human wild type prolactin (Δ41–52).

In another embodiment, a substitution mutation is made by replacing amino acids in one or more of the three regions described above with polar acidic amino acids, such as glutamic acid. Alternatively, amino acids from one or more of the three regions can be replaced by an alanine or phenylalanine, which have non-polar hydrophobic groups that reduce or add bulk, respectively, and disrupt the close packing of the atoms in the hydrophobic clusters.

Replacement of amino acids within the three regions of human prolactin described above can be made with amino acids having uncharged polar R groups, or polar basic amino acids that are positively charged at neutral pHs. Such mutations can produce stable proteins that fold similarly to the native protein but which no longer properly repack the hydrophobic core of the protein in response to site 1 binding, and thus fail to propagate a conformation change that ultimately restructures and turns-on site 2 of prolactin for receptor binding.

Alternatively, additional amino acids can be inserted into the hydrophobic core of the amino acids that propagate the site 1 binding-induced conformation change. Insertion of polar or charged residues (such as glutamic acid) tends to disrupt the spatial arrangement of atoms within the hydrophobic core and disrupt the propagation of a conformational change. Disruption of the conformation change diminishes the site 1-mediated induction of site 2 function.

Prolactin variants of the invention can have the following characteristics:

i) The protein is an effective antagonist. The ability of a mutated or variant prolactin molecule to act as an antagonist can be measured in a variety of ways. Such assays commonly involve incubation of wild-type prolactin with various concentrations of the putative prolactin antagonist, in the presence of prolactin receptors or in the presence of cells that require prolactin for either growth or viability. The assay is such that activity of wild-type prolactin to bind receptor and/or transmit a biological response through the receptor, and the ability of the antagonist to reduce these properties, can be measured. Another type of assay that can be used to determine whether the protein is an effective antagonist is a dose-response assay where prolactin-like activity (a biological response in cells or animals) of the protein is measured at different antagonist concentrations (see FIG. 6). Some prolactin antagonists according to the invention will exhibit a dose-response curve that has an agonist phase that is right-shifted as compared to the curve for wild-type prolactin, and an antagonist phase that is unchanged as compared to the curve for wild-type prolactin.

ii) The protein binds to receptor through site 1 but does not bind to receptor through site 2.

iii) The protein folds properly as compared to folding of wild-type prolactin (i.e., has native folding). Native protein folding is measured by methods that can determine or compare tertiary structure of a protein. Such methods include, but are not limited to, absorption spectroscopy, fluorescence spectroscopy, optical rotary dispersion, circular-dichroism, nuclear magnetic resonance, and electron spin resonance.

iv) The protein has little or no agonist activity. In some embodiments, the inventive protein has less than 1% agonist activity of the wild-type prolactin. The inventive antagonists can have less than 0.095%, 0.090%, 0.085%, 0.080%, 0.075%, 0.070%, 0.065%, 0.060%, 0.055%, 0.050%, 0.045%, 0.040%, 0.035%, 0.030%, 0.025%, 0.020%, 0.015%, 0.010%, 0.005%, 0.001% agonist activity, or even less, as compared to wild-type prolactin. Agonist activity can be measured using a variety of methods. One method utilizes cell lines possessing prolactin receptors wherein binding of wild-type prolactin to the receptors initiates a biological response that is easily measured.

The prolactin variants with antagonist activity can have the additional features of possessing a site 1 that is functional and binds to receptor and a site 2 that is unable to bind receptor, even after site 1 on the protein has bound receptor. Measurements of functioning of the two sites can be performed in assays where one of the two sites is rendered nonfunctional and the functioning of the other site is measured. Some prolactin antagonists of the invention are unable to undergo appropriate conformation changes in response to binding of receptor by site 1 and are therefore unable to bind receptor at site 2.

The present invention also provides methods for treatment of cancers that are prolactin-responsive or prolactin-dependent. Certain breast cancers and prostate cancers are cancers of this type. The methods involve administering to a patient the prolactin antagonists described herein for the purpose of inhibiting the activity of prolactin signaling molecules and inhibiting or killing the cancer cells in the patient. Other cancers treatable in accordance with the present invention include blood cancers, such as leukemias, and other forms of cancer, such as lymphomas.

The present invention also provides methods for suppressing lactation in a female after birth. The method involves administering to female the prolactin antagonists described herein.

The present invention also provides methods for discovering and making antagonists of signaling molecules that bind to receptors using the mechanism described herein—where site 1 binding to a receptor causes a conformational change in the ligand such that site 2 can bind to receptor.

In particular, the present invention provides a modified human prolactin molecule comprising the following amino acid sequence (SEQ ID NO: 1):

LPICPGGAAR CQVTLRDLFD RAVVLSHYIH NLSSEMFSEF 10 20 30 40

DKRYTHGRGF ITKAINSCHT SSLATPEDKE QAQQMNQKDF 50 60 70 80

LSLIVSILRS WNEPLYHLVT EVRGMQEAPE AILSKAVEIE 90 100 110 120

EQTKRLLEGM ELIVSQVHPE TKENEIYPVW SGLPSLQMAD

130 140 150 160

EESRLSAYYN LLHCLRRDSH KIDNYLKLLK CRIIHNNNC 170 180 190 199 wherein the prolactin molecule comprises at least one mutation in a region selected from i) amino acids 41–57, ii) amino acids 94–110, and iii) amino acids 160–173; and wherein the at least one mutation is selected from deletions, replacements, and insertions.

In particular, the prolactin molecule can comprise at least one replacement mutation in region i), ii), and/or iii). In some embodiments, the at least one replacement mutation comprises replacing an amino-acid having a nonpolar or hydrophobic side group, chosen from A, V, L, I, P, F, and M, with a polar acidic amino acid that is negatively charged at pH 6.0-7.0, chosen from D and E. The at least one replacement mutation can be chosen from, for example, F50E, I51E, A54E, I55E, L95E, L98E, V99E, V102E, L165E, L171E, and L172E.

In some embodiments, the at least one replacement mutation comprises replacing an amino acid having an uncharged polar side group, chosen from G, S, T, Y, N, and Q, with a polar acidic amino acid that is negatively charged at pH 6.0–7.0, chosen from D and E. The at least one replacement mutation can be chosen from, for example, T45E, T52E, N56E, S57E, Y96E, Y168E, and Y169E.

In some embodiments, the at least one replacement mutation comprises replacing a polar basic amino acid that is positively charged at pH 6.0–7.0, chosen from K, R, and H, with a polar acidic amino acid that is negatively charged at pH 6.0–7.0, chosen from D and E. The at least one replacement mutation can be chosen from, for example, H46E, R48E, K53E, H97E, and H173E.

In some embodiments, the at least one replacement mutation comprises replacing an amino acid having an uncharged polar side group, chosen from G, S, T, Y, N, and Q, with an amino acid having a nonpolar or hydrophobic side group, chosen from A, V, L, I, P, F, and M. The at least one mutation can be, for example, G47F and/or G49F.

In some embodiments, the at least one replacement mutation comprises replacing a polar basic amino acid that is positively charged at pH 6.0–7.0, chosen from K, R, and H, with an amino acid having a polar nonpolar or hydrophobic side group, chosen from A, V, L, I, P, F, and M. The at least one mutation can be chosen from, for example, H46A and R48A.

In some embodiments, the prolactin molecule comprises at least one deletion mutation in region i), ii), and/or iii). The at least one deletion mutation can comprise, for example, a single deletion of an amino acid chosen from amino acids 41, 42, 43, 44, 45, 46, 47, 48, 49, 50, 51, 52, 53, 54, 55, 56, 57, 94, 95, 96, 97, 98, 99, 100, 101, 102, 103, 104, 105, 106, 107, 108, 109, 110, 160, 161, 162, 163, 164, 165, 166, 167, 168, 169, 170, 171, 172, and 173. In some embodiments, the at least one deletion mutation comprises a deletion of F50.

In other embodiments, the at least one deletion mutation comprises deletion of more than one amino acid chosen from, for example, amino acids 41, 42, 43, 44, 45, 46, 47, 48, 49, 50, 51, 52, 53, 54, 55, 56, 57, 94, 95, 96, 97, 98, 99, 100, 101, 102, 103, 104, 105, 106, 107, 108, 109, 110, 160, 161, 162, 163, 164, 165, 166, 167, 168, 169, 170, 171, 172, and 173. The at least one deletion mutation can comprise, for example, a deletion of amino acids chosen from 41–57, 94–110, 160–173, 41–49, 50–57, 41–42, 41–43, 41–44, 41–45, 41–46, 41–47, 41–48, 41–50, 41–51, 41–53, 41–54, 41–55, and 41–56. In some embodiments, the deletion is not of amino acids 41–52.

In some embodiments, the modified human prolactin molecule comprises at least one insertion mutation in region i), ii), and/or iii).

The invention also is directed to modified human prolactin molecules that exhibit the following characteristics: 1) exhibits antagonist activity; 2) binds to prolactin receptor through site 1; 3) does not bind to prolactin receptor through site 2 or has greatly diminished binding through site 2; and 4) exhibits less than 1% of unmodified prolactin's agonist activity. The prolactin molecule can exhibit less than 0.9% of unmodified prolactin's agonist activity, and less than 0.5% of unmodified prolactin's agonist activity.

The invention is also directed to pharmaceutical compositions comprising the modified human prolactin molecule described herein, and at least one pharmaceutically acceptable excipient.

The invention is also directed to methods of treating a cancer comprising administering an effective therapeutic amount of the modified human prolactin molecules described herein. The cancer can be breast cancer and it can be leukemia.

The invention is also directed to methods for reducing or suppressing lactation comprising administering an effective therapeutic amount of the modified human prolactin molecules described herein.

BRIEF DESCRIPTION OF THE DRAWINGS

The present invention may be more readily understood by reference to the following drawings wherein:

FIG. 1 shows two illustrations of folded backbone/ribbon structure of human prolactin as determined by nuclear magnetic resonance (Protein Data Base # 1N9D), highlighting the four-helix bundle topology. The illustration in the upper frame is a side view of the protein showing helices 1 through 4 as ribbons. Black arrows show the direction of the helices with the arrows pointing to their C-terminus. Mini-helix 1, the N- and C-termini of the protein are labeled. The lower frame of the figure is a slab that has been cut from the lower portion of the protein shown in the upper frame. Site 1 (between helices 1 and 4) and site 2 (between helices 1 and 3) for receptor binding are illustrated.

FIG. 3 shows the polynucleotide sequence (SEQ ID NO: 2) of human prolactin messenger RNA using single letter abbreviations for the four nucleotides (a, c, g, t). This sequence is Genbank accession No. BC015850. The TTG codon, shown in bold type in the sequence, is the codon encoding the first bolded amino acid in FIG. 4 (leucine) which is the first amino acid in the mature form of human prolactin isolated from the pituitary.

FIG. 4 shows the amino acid sequence (SEQ ID NO: 3) of the precursor form of the human prolactin protein in single letter abbreviations for the amino acids encoded by the polynucleotide sequence shown in FIG. 3. The amino acid sequence is Genbank accession No. NP 000939. This is the form produced in various human tissues. The non-bolded signal sequence is cleaved from the precursor protein prior to its folding, leaving the mature form (the bolded sequence of amino acids) that can subsequently be secreted from its cell of origin.

FIG. 5 shows the amino acid sequence (SEQ ID NO: 4) of recombinant wild-type human prolactin as prepared by our group. The signal sequence has been eliminated by removal of the nucleic acids that would code for this sequence of amino acids. The sequence pictured includes the bolded amino acids of FIG. 4 with an additional amino acid, a methionine, added to the N-terminus of the protein. The amino acid following the N-terminal methionine (leucine) is referred to as amino acid I in this specification. The amino acids following this L (leucine) are numbered consecutively, starting with amino acid 2 (P). The three regions containing amino acids designated in bold type are the approximate locations of regions of the prolactin molecule in which mutations produce antagonists (amino acids 41–57, 94–110, and 160–173) by corruption of the residues that participate in propagating the binding-induced conformation change.

FIG. 10 shows the relative binding capacities of human prolactins that have been blocked at site 1 (K181 C) or site 2 (G129C) or not blocked (M158C). Binding is followed by surface plasmon resonance techniques. Strategically located cysteines couple these human prolactins by disulfide bonds through positions that block site 1 (K181C), block site 2 (G129C) or block neither site 1 nor site 2 (M158C).

Figure 2:
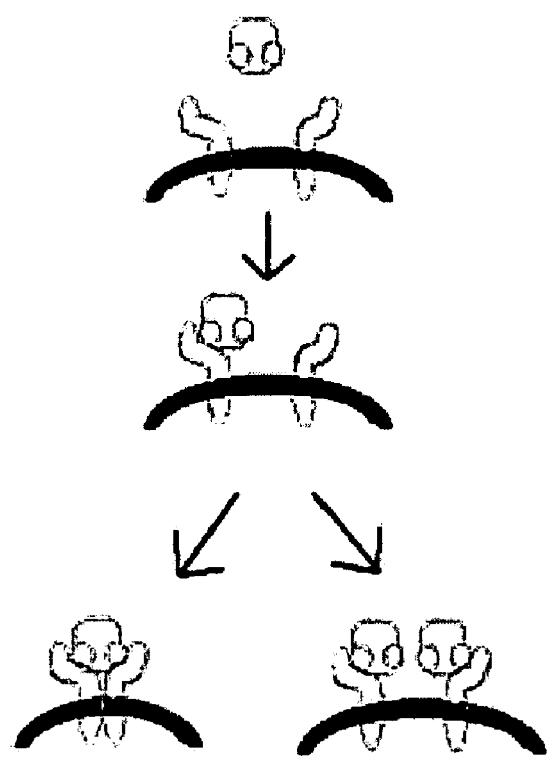
FIG. 2 diagrammatically illustrates the mechanism by which prolactin binds to its receptor. Soluble prolactin first binds one receptor through site 1. This site-1 binding induces a conformation change, which organizes site 2 and allows subsequent binding of a second receptor through site 2. Formation of these heterotrimeric complexes induces the agonist action of the hormone within the target cell. In the presence of extremely high concentrations of human prolactin only 1 to 1 heterodimeric complexes are formed. In this situation, no trimers are formed and human prolactin functions as an antagonist.

This experimental design compares the magnitudes of prolactin receptor binding to human prolactins where site 1, site 2, or neither sites were structurally blocked. The binding was conducted from time 0 to approximately 250 seconds with a high saturating concentration (100 $\mu$M) of the extracellular domain of the human prolactin receptor being slowly flowed over the fixed hormones on the surfaces of the optical device. Thus, the initial binding and the equilibrium binding at saturating receptor concentrations were followed. After binding equilibrium was achieved buffer without receptor was flowed over the prolactins and the dissociation of the receptors from the prolactins was followed.

After a saturating equilibrium was achieved (upper panel) the human prolactin bound to the optical surface through cysteine 158 showed a signal that upon calculation described a stoichiometry of 2 receptors bound to each prolactin (lower panel). When human prolactin was bound to the optical surface through a cysteine located at residue 129 the stoichiometry was approximately a 1 to 1. This shows that when site 2 is blocked, that site 1 can bind receptor. Most importantly, when human prolactin is bound by a disulfide bond placed within site 1 (cysteine 181) little receptor binding is observed. This observation indicates that site 2 binding is dependent on binding at site 1. Thus, site 1 binding is required to open or create site 2. This information shows that site 1 is functionally coupled to site 2, and implies that site 1 binding must induce a change of conformation to create the structural geometry that will provide function to site 2.

Figure 11:
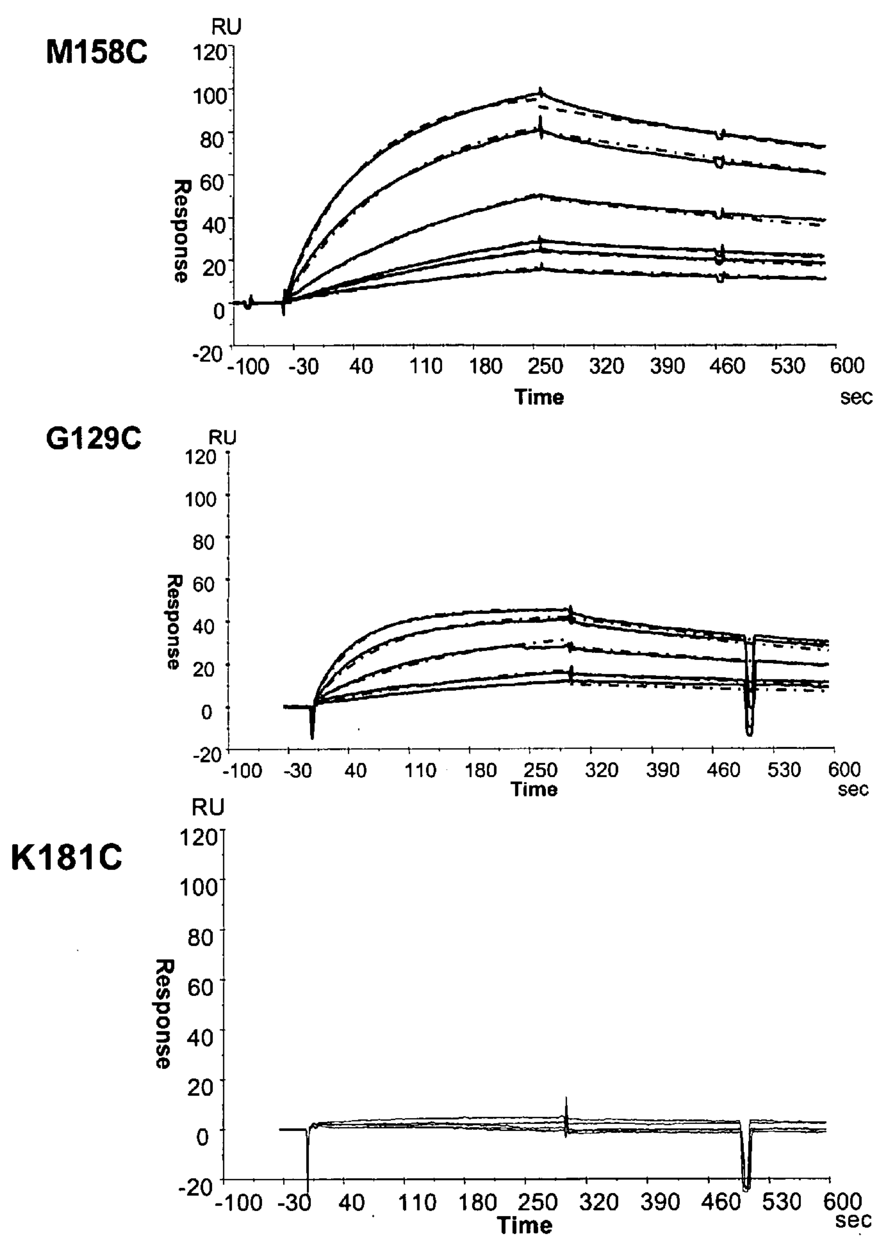

FIG. 11 shows the binding kinetics of the extracellular domain of the human prolactin receptor to human prolactins followed by surface plasmon resonance. Surface plasmon resonance binding kinetics of human prolactin coupled by residue 129, 158, or 181 and exposed to increasing concentrations of the extracellular domain of the human prolactin receptor. The relative magnitudes of receptor binding as well as the shape of the binding curves suggest that site 1 (coupled through 129C) binds through simple single site binding model, while binding at site 2 (coupled through 181C) does not occur when site 1 is not available for receptor binding. Finally, when both receptor sites of human prolactin are available (coupled through 158C) a complex binding curve is observed and a larger amount of receptor is bound. Association and disassociation rate constants were calculated from this data and are provided in Table 1.

Figure 12:
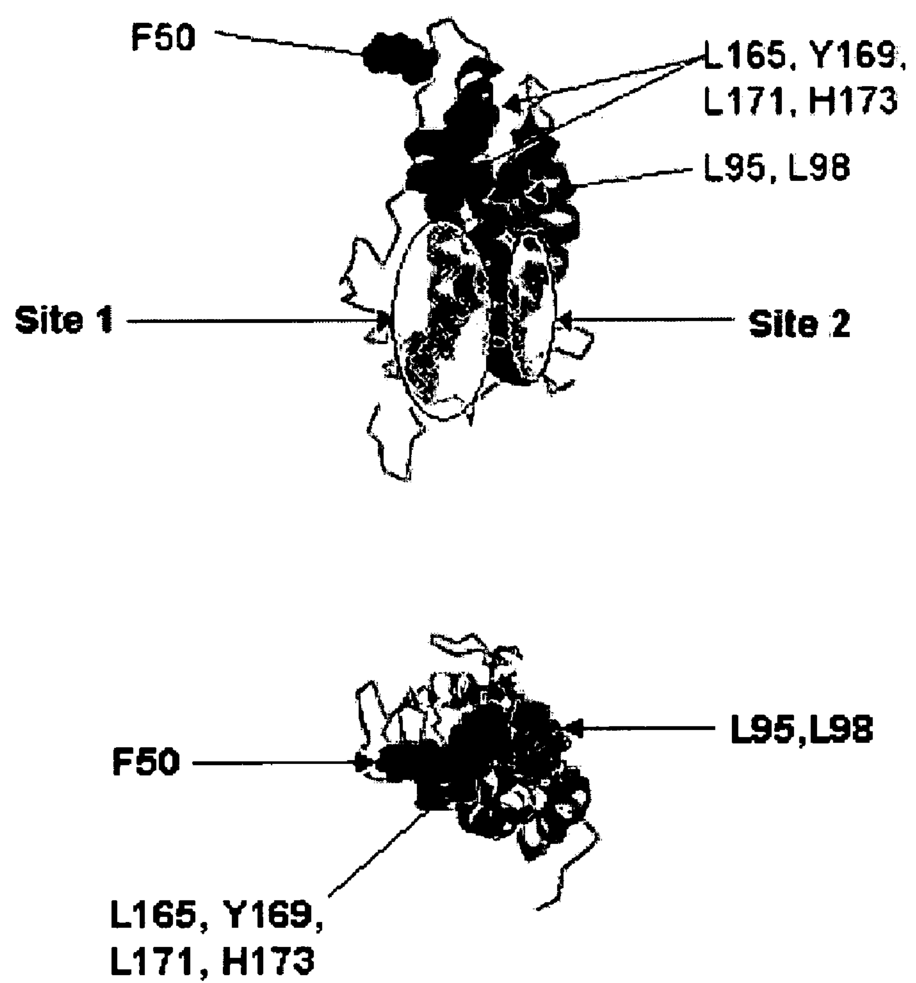

FIG. 12 diagrammatically illustrates a backbone model of human prolactin (Protein Data Base # 1N9D), highlighting the residues that were identified by mutagenic experiments to be required for the transmission of the site 1 binding-induced conformation change (Table 2). The upper figure shows the side view of human prolactin with sites 1 and 2 shown as circled areas. The residues required for propagation of the site 1 binding-induced conformation change are shown in spacefill model and identified. The lower figure is a top view of the same model showing the articulation of the residues across the interior of the molecule.

Figure 13:
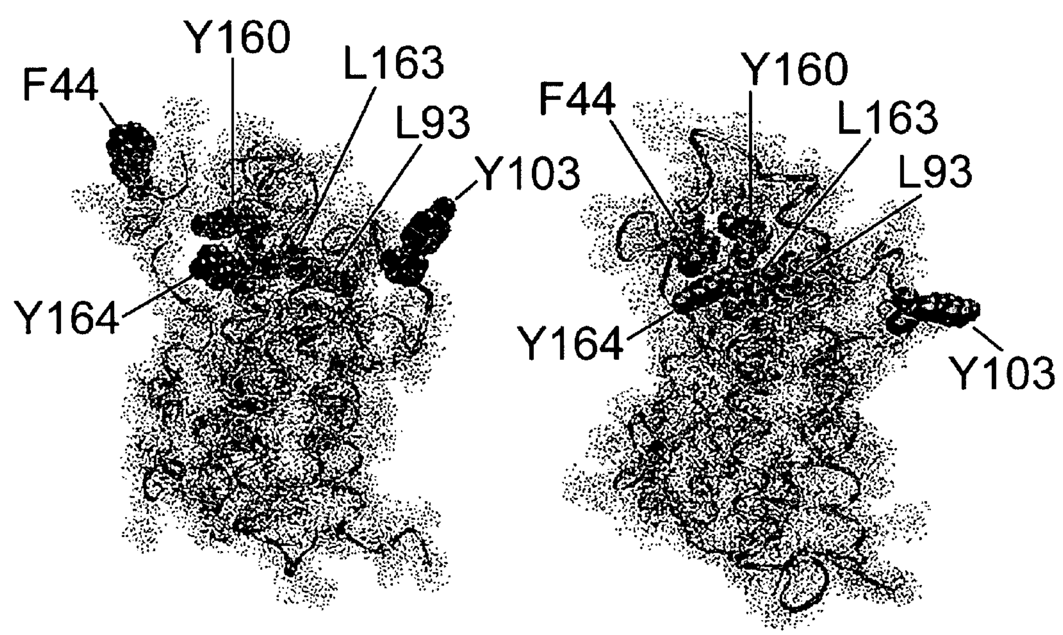

FIG. 13 shows a model of human growth hormone when free of prolactin receptor (left, Protein Data Base # 1BP3) or bound to an extracellular domain of the human prolactin receptor at site 1 (right, Protein Data Base # 1HGU). Residues were identified in mutagenic experiments that were required for the site 1 binding-induced propagation change (Table 3). These residues are shown in a spacefill model. Note that upon prolactin receptor binding at site 1 of human growth hormone the residues contained in the conformation motif change their spatial organization.

Figure 14:
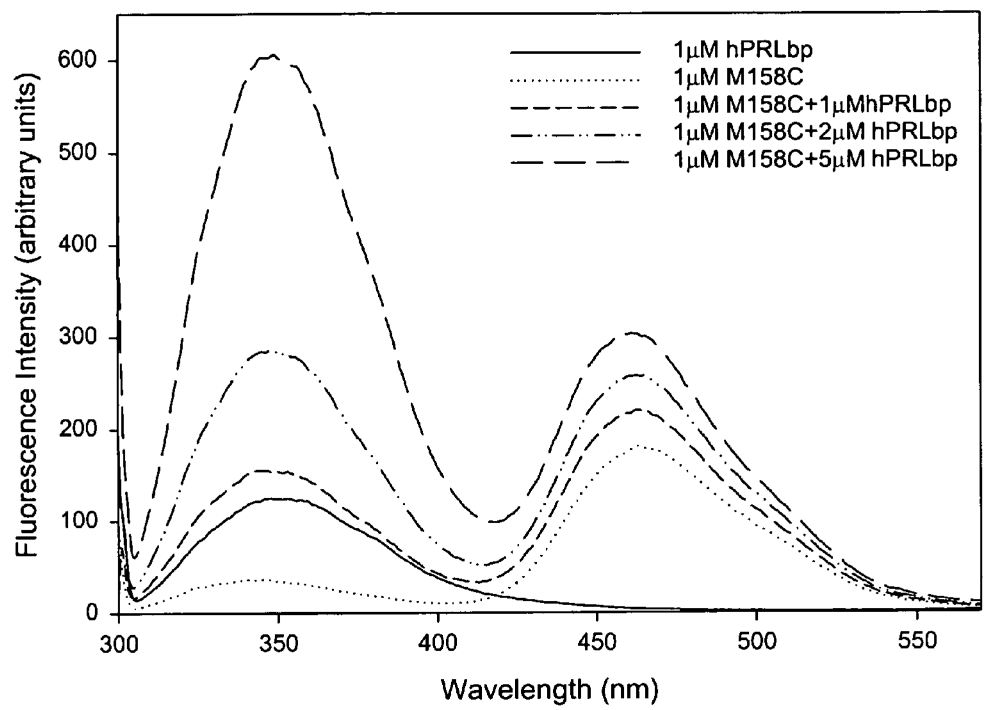

FIG. 14 shows the results of a fluorescence resonance energy transfer (FRET) study. The efficiency of a radiationless energy transfer from tryptophans (positions 91 and 150 in human prolactin) to a coumarin fluorophore positioned at residue 158 is measured. Binding of the coumarin-labeled human prolactin by the extracellular domain of the human prolactin receptor increased the energy transfer and subsequent coumarin fluorescence (around 469 nm). The efficiency of energy transfer is inversely proportional to the $6^{th}$ power of the average distance between tryptophans and the coumarin reporter. This data is physical evidence indicating that human prolactin, when bound by a prolactin receptor, undergoes a conformation change that brings the coumarin and the tryptophans into closer proximity. Note the increases in fluorescence at approximately 350 nm are a result of the tryptophan contained in the increasing concentrations of prolactin receptor added to the binding reactions.

Figure 15:
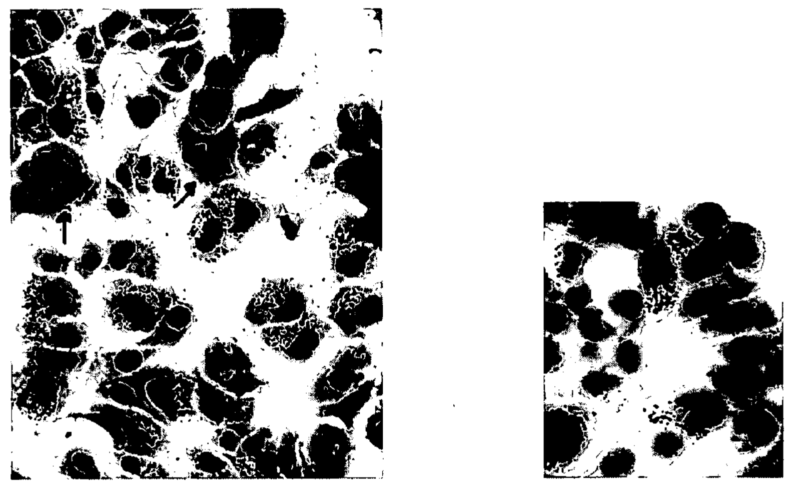

FIG. 15 shows a photomicrograph of T47D human breast cancer cells after initiation of apoptosis by treatment with Δ41–52 human prolactin. Left picture shows cells treated for 48 hours with Δ41–52 human prolactin (600× magnification). Right picture shows cells treated for 48 hours with wild-type human prolactin (600× magnification). Arrows identify nuclei undergoing fragmentation, a late stage of apoptosis.

Figure 16:
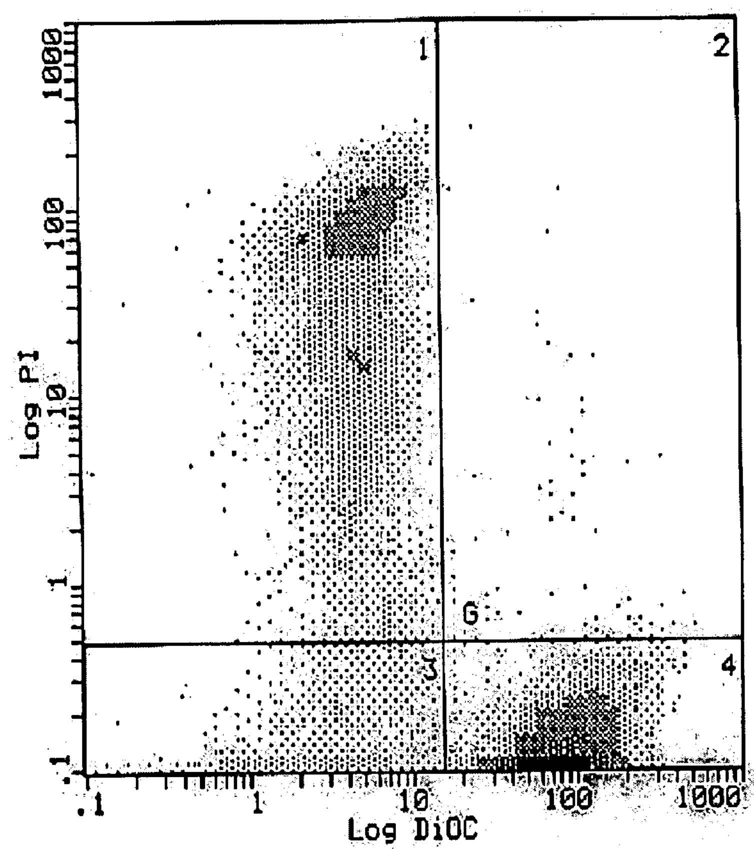

FIG. 16 shows the DiOC (X-axis) and PI (Y-axis) fluorescence from Jurkat cells for a single culture with defined hormone dose and treatment time. Note that both scales are logarithmic. This figure is representative of data in the experiments described in Example 10. Each dot represents the data from a single cell. Normal healthy cells are primarily found in quadrant 4 (lower right) and have low PI and high DiOC signals. Cells undergoing apoptosis are found in quadrant 3 (lower left), have a reduced DiOC signal, and retain a low PI signal. Finally, dead cells (those completing the apoptotic process) are found in quadrant 1 (upper left) and retain a low DiOC signal but have an increased PI signal. The boarders of the quadrants are the same for all cultures in a single experiment. The cells in each quadrant are expresses as a percentage of the total and are displayed in FIGS. 17 and 18.

Figure 17:
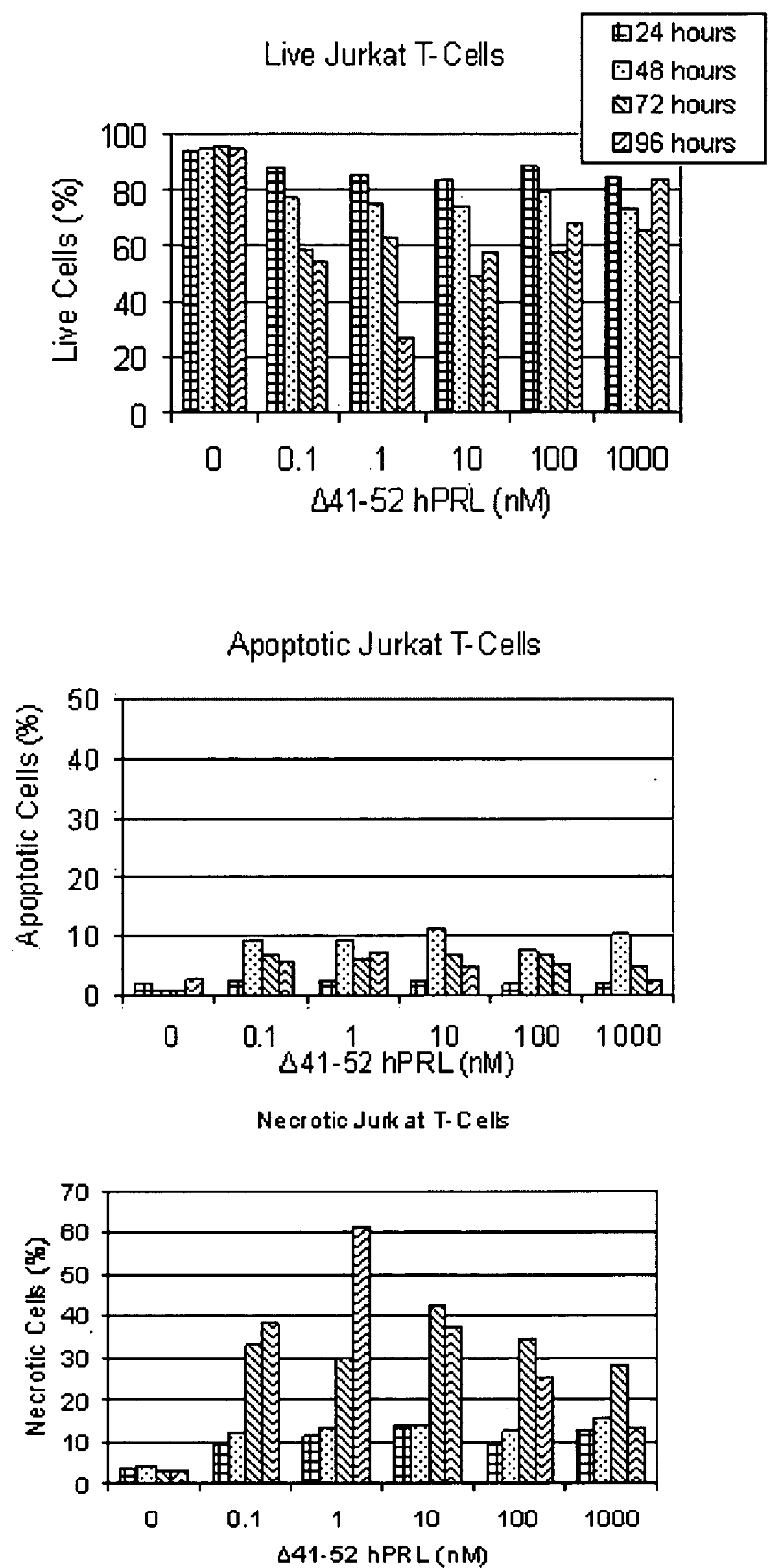

FIG. 17 shows the dose and time dependence of the viability of Jurkat cells (derived from a human T-cell leukemia) when treated with Δ41–52 human prolactin antagonist. The effects of both time of treatment and concentration of Δ41–52 human prolactin for live, dead, and apoptotic cells are shown. The data show that treatment of Jurkat cells with 1 nM of Δ41–52 human prolactin leaves only 25 to 30% of the total cells alive after a 96-hour treatment.

Figure 18:
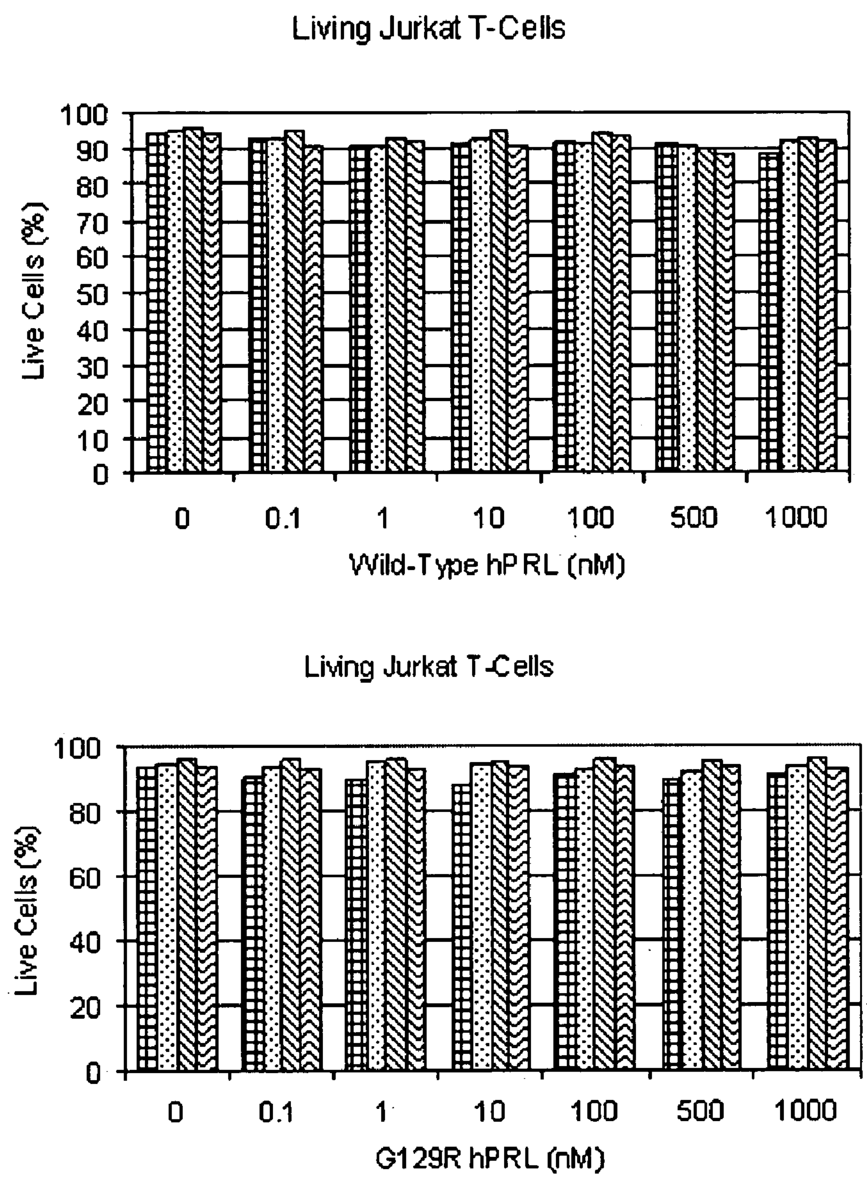

FIG. 18 shows control experiments for Jurkat cells. Treatment of Jurkat cells for up to 96 hours with up to 1000 nM of either wild-type human prolactin or the antagonist G129R human prolactin do not affect the percent of living cells. Note that G129R human prolactin is the best characterized and most potent antagonist in the class that uses steric blockage of site 2 to reduce the affinity of the hormone for receptor at site 2 but has little to no effect on the cell viability.

DETAILED DESCRIPTION OF THE INVENTION

The present invention will now be described, with occasional reference to the accompanying drawings, in which specific embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise. All publications, patent applications, patents, and other references mentioned herein are incorporated by reference in their entirety.

The present invention is based on the finding that binding of certain hormones, including prolactin, to receptors through site 1, causes a conformational change in the hormone such that site 2 can bind to the receptor (FIG. 2). In this induced-fit dimerization mechanism, site 1 on the ligand first binds to one molecule of receptor. Before site 1 binds to receptor, site 2 is not available to bind to the receptor. After site 1 on the hormone binds receptor, then site 2 becomes available to bind receptor. Site 2 then binds a second lactogenic receptor. This second binding event creates a biologically active dimer pair of receptors that may stimulate target the cell.

The present invention is discussed with regard to prolactin but other hormones are contemplated. In particular, growth hormone, which involves a similar, if not identical, mechanism of action, is contemplated. Thus, mutations that can be made to prolactin can also be made to growth hormone, with expected results being similar. Placental lactogen, and other interleukins, are also within the scope of the present invention.

With respect to prolactin and other lactogenic hormones, a portion of the chemical energy derived from binding of site 1 of the hormone to the receptor is used to induce and propagate across the molecule a change in conformation (a rearrangement of the atoms) that results in a structuring of the atoms on the opposite side of the molecule, creating the second receptor-binding site (site 2). This second receptor-binding site of the hormone is then available to bind a second lactogenic receptor to form a receptor dimer that is known to be the biologically active form of the receptor.

Described herein are amino acid regions in prolactin (and growth hormone and other similar hormones), outside of site 1 and 2, that are necessary for site 2 on the hormone to become available to bind receptor after site 1 on the hormone has already bound receptor. Prolactin mutants are described that have substitutions or deletions of amino acids in these regions, such mutant prolactin molecules being antagonists that have reduced agonist activity.

The approach that was used to identify the mechanism of prolactin binding to receptor, identifying the regions of prolactin necessary for the conformation change, and for identifying mutations within the molecule that yield antagonists is described as follows.

In the first step, a polynucleotide sequence encoding the ligand is used. Mutations are introduced into the polynucleotide, in some embodiments using site-directed mutagenesis techniques. There are a variety of such techniques that are well known in the art. These methods commonly involve biochemical manipulation of the polynucleotide in vitro to specifically alter the polynucleotide sequence. Thus, while site-directed mutagenesis is mentioned here, other techniques are contemplated and within the scope of the invention.

The altered polynucleotide is then isolated. Finally, the nucleotide sequence of the product is confirmed by automated chemical methods common to the art to confirm the presence of the desired mutation within the sequence constituting the wild-type polynucleotide.

In one embodiment, polymerase chain reaction ("PCR")-based site-directed mutagenesis is used. Such technique allows for deleting amino acids, adding amino acids, or substituting for amino acids in the wild-type or other sequences. In PCR-based site-directed mutagenesis a DNA molecule encoding a wild-type or other ligand amino acid sequence is ligated into a cloning vector and used as a template. Vector-specific primers and oligonucleotide primers designed to encode the changes, i.e., the deletions, additions, and/or substitutions, sought to be introduced into the gene are used during amplification to provide DNA molecules containing the desired modified gene dr polynucleotide. DNA molecules containing the modified polynucleotide are isolated from the PCR products using conventional methods.

Other techniques can be used. One such technique whose use is described in the Examples of this application is the Kunkel method. The Kunkel method is described in a number of publications (Kunkel, T. A., *Proc. Natl. Acad. Sci. USA* 82: 488–492 (1985); Kunkel, T. A., Roberts, J. D. and Zakour, R. A., *Methods in Enzymology* 154:367–382 (1987)).

It should be noted that multiple mutations can be made to effect a change in the protein. For example, substitutions can be combined with deletions or insertions. The possibilities are not limited by this disclosure and one skilled in the art would understand, based on the present disclosure, what combinations could be made to achieve the desired effect.

With respect to human prolactin, mutations can be made in polynucleotides that encode the following three regions of the molecule (numbering of the amino acids referred to below is as shown in FIG. 5 and the brief description of FIG. 5):

i) amino acid residues of approximately 41–57. Amino acids 41–57 comprise a region of the human prolactin molecule located between the C-terminus of helix 1 and the disulfide bond at amino acid residue 58. The region includes mini-helix 1. The ends of this region are covalently linked to the end of helix 1 through the backbone peptide bonds and to helix 4 by the disulfide formed between cysteines 58 and 174. These attachments help fix these amino acids and provide outer limits to their mobility. Helices 1 and 4 are relatively compact and rigid. The amino acid residues between amino acids 41 and 57 are relatively mobile, based on models and homologies to the X-ray crystallographic structures of human growth hormone and a nuclear magnetic resonance structure of human prolactin. Their mobility allows some of these amino acids to propagate a conformation change when constrained by the presence of the receptor binding to site 1. The amino acid in positions 50 to 57 are closer to site 1 and their function may be more directly associated with the spatial constraints imposed by receptor binding at site 1. The amino acid residues approximately 41–49 are more distal to site 1 and are believed to be associated with those that propagate the conformation change. Thus, mutations in this region are can be directed at amino acids 41–49.

ii) amino acid residues of approximately 94 to 110. This region is located between a proline-induced break in helix 2, at proline 94, and alanine 111, which marks the beginning of helix 3. This region is also relatively mobile. As judged by NMR studies with human prolactin and structural homologies to X-ray crystallographic structures of human growth hormone either free from the effects of receptor binding or bound by a human lactogenic receptor at site 1, this region is non-helical when the ligand is not receptor bound but forms a helix when bound by the human lactogenic receptor. Based on homology modeling it is believed that site 1 binding leads to the extension or stabilization of helix 2. Thus, this area of the protein is transformed from a relatively mobile to a more compact rigid structure as a result of lactogenic receptor binding at site 1 of human prolactin.

iii) amino acid residues of approximately 160 to 173. This region is located in the N-terminus of helix 4 preceding cysteine 174 (this is the cysteine that forms a disulfide bond with cysteine 58, adjoining region 41–57).

It is important to recognize that the regions set forth herein, i.e., regions i, ii, and iii, are purposefully defined by approximation. That is, for example, region iii comprises approximately amino acid residues 160–173. However, the role any individual amino acid plays in protein folding and function is not entirely precise, and cannot be entirely known. Thus, it is expected that, for example, in region iii, residues 159 or 174 may also be involved; in region ii residues 93 and 111, for example, may be involved; in region i, residues 40 and 58, for example, may be involved. And again, these are only examples—other amino acids may be determined to be involved in this mechanism of action. Those of skill in the art will recognize what modifications can be made to create mutations according to this invention.

It should also be noted that while human prolactin is the example mentioned frequently throughout this disclosure, modified prolactins from other animals are contemplated. Modified growth hormones from humans, as well as other animals, are also contemplated.

The types of mutations that are made are of various types. Deletion mutations, in which certain amino acids are removed from the sequence can be made. Insertion mutations can also be made. And mutations that result in substitutions of one amino acid for another can also be made. Again, the types of mutations can be combined to achieve the desired affect.

With regard to amino acid substitutions, a variety of amino acid substitutions can be made. As used herein, amino acids generally can be grouped as follows: (1) amino acids with nonpolar or hydrophobic side groups (A, V, L, I, P, F, W, and M); (2) amino acids with uncharged polar side groups (G, S, T, C, Y, N, and Q); (3) polar acidic amino acids, negatively charged at pH 6.0–7.0 (D and E); and (4) polar basic amino acids, positively charged at pH 6.0–7.0 (K, R, and H).

While the naturally occurring amino acids are discussed throughout this disclosure, non-naturally occurring amino acids, or modified amino acids, are also contemplated and within the scope of the invention. In fact, as used herein, "amino acid" refers to natural acids, non-naturally occurring amino acids, and amino acid analogs, all in their D and L stereoisomers. Natural amino acids include alanine (A), arginine (R), asparagine (N), aspartic acid (D), cysteine (C), glutamine (Q), glutamic acid (E), glycine (G), histidine (H), isoleucine (I), leucine (L), lysine (K), methionine (M), phenylalanine (F), proline (P), serine (S), threonine (T), tryptophan (W), tyrosine (Y) and valine (V). Non-naturally occurring amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2 -aminopimelic acid, 2,4 diaminoisobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine, and pipecolic acid.

After classifying candidate amino acids within the three regions described above and examining their location in model 3-dimensional structures of human prolactin (e.g., FIG. 1), we noted that the amino acids of these three portions of the protein articulated with each other, implying their chemical interaction in the protein structure. Secondly, we observed that many of these amino acids were hydrophobic residues, which would pack within the center of the molecule and which would need to rearrange themselves specifically during a conformation change. Based on these observations, we have created the following strategy in choosing which amino acids to delete or mutate and what amino acid to substitute for the wild-type amino acid.

As used herein, substitution mutations are designated by a code consisting of a letter, a number and another letter (e.g., F50E). In this code, the first letter indicates the identity of the amino acid in the wild-type prolactin molecule (F is phenylalanine). The number in the code indicates the location of the amino acid (50 is the 50th amino acid in the protein from the N terminus, numbered as in FIG. 5). The last letter in the code indicates the identity of the amino acid that is substituted in the particular variant (E represents glutamic acid replacing phenylalanine at position 50 in the protein).

In certain of the specific variants, we chose to replace hydrophobic residues within these regions. In some embodiments, these amino acids are replaced with glutamic acid (E) a member of group 3 described above. Examples of such variants that have been made are F50E, I51 E, A54E, I55E, L95E, L98E, V99E, V102E, L165E, L171E and L172E. Of course, aspartic acid can also be used.

In other specific variants, amino acids with uncharged polar side groups have been replaced, in some embodiments, with glutamic acid. Examples of such variants that have been made are T45E, T52E, N56E, S57E, Y96E, Y168E and Y169E. Aspartic acid can also be used.

In other specific variants, polar basic amino acids that are positively charged at pH 6–7 have been replaced, in some embodiments, with glutamic acid. Examples of such variants that have been made are H46E, R48E, K53E, H97E and H173E. Aspartic acid can also be used.

Glutamic acid normally carries a negative charge in the terminal carboxyl group of its side chain and introduces a polar environment when it packs into the interior of the protein. A secondary consideration was the size of the substitution placing a significantly greater or lesser atomic mass in place of an "average" hydrophobic residue might lead to a completely misfolded protein. Thus, glutamic acid substitution was a reasoned compromise. We reasoned that introduction of a polar residue in this hydrophobic environment would not allow a completely native fold in this region of the protein and would corrupt the changes in local folding inherent in the propagation of a site 1 binding-induced conformation change. We designed our changes to achieve this local disruption without creating a global change in the protein that would affect either receptor binding sites, particularly site 1. Using this strategy we have created numerous mutations in these three regions of human prolactin.

As noted above, aspartic acid can also be used to effect similar changes. Also, other amino acids with polar character can be introduced into this hydrophobic environment to prevent a completely native fold in this region of the protein, thereby corrupting the changes in local folding inherent in the propagation of a site 1 binding-induced conformation change.

In other specific variants, amino acids with uncharged polar side groups were replaced with phenylalanine (e.g., G47F and G49F). Other uncharged polar groups that can be targeted include S, T, C, Y, N, and Q. These residues can be replaced with amino acids having nonpolar or hydrophobic side groups, such as A, V, L, I, P, F, W, and M.

In other variants, polar basic amino acids that are positively charged at pH 6–7 have been replaced with alanine (e.g., H46A and R48A). Polar basic amino acids include, but are not limited to, K, R, and H. Other amino acids having nonpolar or hydrophobic side groups, besides A, include F, V, L, I, P, W, and M.

Other mutations include deletions of amino acids from one or more of regions i) amino acids 41–57, ii) amino acids 94–110, and iii) amino acids 160–173. For example, any combination of amino acids 41, 42, 43, 44, 45, 46, 47, 48, 49, 50, 51, 52, 53, 54, 55, 56, 57, 94, 95, 96, 97, 98, 99, 100, 101,102, 103,104,105,106, 107, 108, 109, 110, 160, 161, 162, 163, 164, 165, 166, 167, 168, 169, 170, 171, 172, and 173 can be deleted (without adding an amino acid in its place). Examples of mutations of multiple amino acids include deletion of residues 41–57, 94–110, and/or 160–173. Other examples include deletion of 41–49 or 50–57. Other examples include, but are not limited to, 41–42, 41–43, 41–44, 41–45,41–46,41–47, 41–48,41–50, 41–51, 41–52, 41–53,41–54, 41–55, and 41–56. Obviously, space and practicality limits the examples that can be set forth herein.

It should also be noted that the disclosure of each of these embodiments is intended to encompass a collection of the embodiments with any one or more of the embodiments omitted. For example, the invention encompasses deletions of amino acids from one or more of regions i) amino acids 41–57, ii) amino acids 94–110, and iii) amino acids 160–173, with the proviso that the deletion not be of any combination of amino acids set forth in the preceding paragraph. Thus, for example, it is specifically contemplated that the invention encompasses all deletions set forth above, with the proviso that the deletion is not of amino acids 41–52.

After confirming the presence of the desired changes to the sequence of the polynucleotide coding for the desired protein, we prepared the various mutant human prolactins by recombinant DNA technologies and purified and characterized the proteins by methods that are standard to the practice of protein chemistry. We used spectroscopic methodologies to confirm that the structural folding of these proteins has not been dramatically changed by specific mutations and we have screened these proteins to determine their potential as antagonists in biological assays previously described above. These assays are subsequently described in detail.

Expression of protein encoded by the polynucleotide sequence is commonly performed by a variety of methods known in the art. The expression may be done in an in vitro system for coupled transcription and translation. The expression may also be performed in vivo using one of various protein expression systems using cells or viruses. For example, the polynucleotide may be cloned into a bacterial plasmid, introduced into bacteria, and expressed as a protein within the bacteria. In another method, the polynucleotide is cloned into a recombinant virus and the virus is used to infect host cells wherein the protein is produced. Other systems, such as yeast and baculoviruses, also can be used.

After the polynucleotide sequence is expressed as messenger RNA and translated into protein, the over-expressed protein can be isolated and/or purified away from at least some of the contaminating proteins present in the extracts from either the in vitro expression system of extracts from cells or viruses. Examples of methods for protein isolation and purification are well known in the art and may include, for example, chromatographic, electrophoretic, and immunological methods. Similarly, there are varieties of methods known in the art for determining the purity of proteins subjected to these techniques.

Assays to characterize the structure of the protein may be of a variety of types. Physical assays may include spectroscopic methods such as those to determine the absorption (ultraviolet) spectra and/or emission (fluorescence) spectra, optical rotary dispersion, circular dichroism, nuclear magnetic resonance, electron spin resonance, and the like. Hydrodynamic methods such as sedimentation, partial specific volume, diffusion coefficient, and viscosity may also be used. The thermal stability of the proteins also can be measured and used to characterize proteins. Such techniques are well known in the art and are commonly used to compare parameters of the mutant protein with the same parameters of the wild type or un-mutated protein.

The proteins can also be characterized for their ability to bind to their cognate receptors. Methods used to assay for binding are those that can be used in such a way to distinguish between binding by site 1 and binding by site 2 of the ligand. In one type of assay, a BIACORE™ instrument is used (http://www.biacore.com/home.lasso) which measures both the rate and extent of ligand-receptor binding by using surface plasmon resonance. In this procedure, binding of the mutant protein to receptor is characterized by immobilizing the protein on dextran-coated chip surfaces by ligand thiol coupling. The thiol group forms a disulfide bond with a cysteine in the protein and the chemically modified dextran whiskers on the optical chip surface.

Three different variations of experiments can be performed to assay a single mutant. In each of the three variations, the thiol group is attached to a different region of the mutant ligand protein. In one variation, the thiol is attached to a cysteine within site 1, rendering this site unable to bind receptor. In another variation, the thiol is attached to a cysteine within site 2, rendering this site unable to bind receptor. In the third variation, the thiol is attached to a cysteine in a region of the protein that is not within site 1 or site 2, leaving both sites functional and capable of binding receptor. By assaying each of the three different variations for ability to bind to receptor in the BIACORE™ assay, a determination of the functionality of site 1 and site 2 can be made. Using the BIACORE™ instrument, quantitative measurements of the amount of receptor bound by the proteins attached to the chip in each of the three ways can be determined over the time course of the procedure. More specifically, equilibrium binding, time-dependent binding kinetics, and kinetic rate constants can be measured or calculated. Measurements of these parameters using various prolactin mutants are shown in the Examples sections herein.

Assays can be used to measure the ability of the mutant ligands to function as signaling molecules and produce a biological response. This can be done in a variety of ways. In one method, a cell line possessing receptors to which the ligand to be tested can bind is used. Such cell lines are engineered so that binding of the ligand to the receptor in such a way that the appropriate signal transduction pathways are stimulated, produces an output that can be easily measured. Such an output may be expression of a detectable marker gene driven by a transcriptional promoter known to be stimulated by the ligand. In one embodiment, the mutated ligands have no or little agonist activity as compared to the un-mutated ligand.

Assays are also used to determine the antagonist activity of the mutant ligand. Such assays are designed to determine if the putative antagonist is able to prevent the production of a biological response by a wild-type ligand. The inventive antagonists may be able to bind to receptor through its site 1, be unable to bind to receptor through its site 2, have no agonist activity of its own, and be able to prevent signaling by un-mutated agonist. Assays for antagonist activity commonly involve systems in which both the putative antagonist and the wild-type agonist are added to receptors in various proportions and the amount of agonist activity from the wild-type protein is measured. In one type of assay, the wild-type agonist is labeled (labeling with either a radioactive or fluorescent compound are common to the practice of protein chemistry) while the putative antagonist is unlabeled. Both molecules are added and the amount of binding of the wild-type agonist bound to the receptor is determined through measurement of amount of the label associated with the receptors. In other assays, rather than measurement of binding to receptor, a biological response due to agonist may be measured. Such an assay may be performed using above described cell lines with receptors such that binding of agonist to the receptor results in an easily measurable response.

Figure 6:
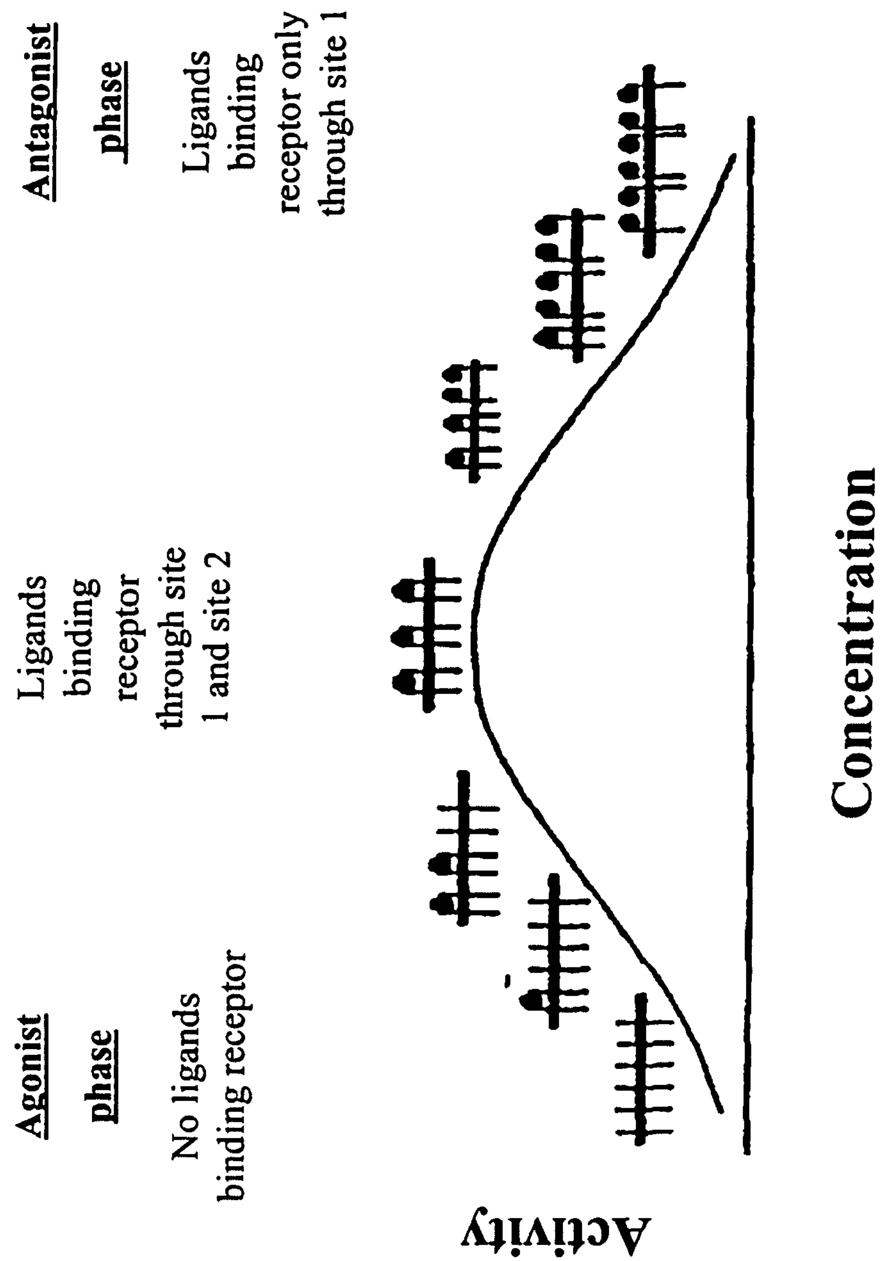
FIG. 6 is an idealized graph to illustrate the relationship between biological activity and hormone concentration for hormones that use a receptor dimerization mechanism. The biological (Y-axis) is plotted against concentration of ligand (X-axis) for a site 1 receptor binding-induced system as described here. The graph shows that biological activity increases as increasing amounts of ligand are added (agonist phase). Maximum activity is obtained as the point where the optimum number of ligands is bound to receptors through both site 1 and site 2 to maximally stimulate the cell. As the concentration of ligand is increased from this point of maximum activity, the increased concentration of ligand depletes the unbound population of receptors that results in an increasing proportion of ligands binding to receptor only through site 1. Biological activity correspondingly decreases (antagonist phase). At the highest concentration of ligand, all ligands bind to receptor through site 1 only and biological activity is returned to baseline levels.

Ligands that possess a site 1 and site 2 for binding to receptor may display self-antagonism in response to increasing concentrations of ligand (FIG. 6). In the case of prolactin, such an assay can be performed, for example, using a cell line possessing prolactin receptors in which growth of the cells is prolactin-dependent and can be measured. Such cell growth is a measure of prolactin activity. In the cases where an antagonist with site 2 partially or completely blocked, the bell-shaped does-response curve (shown in FIG. 6) is shifted downward, influencing neither the prolactin doses required to achieve stimulation or inhibition of cell growth. In contrast, physically blocking site 1 shifts the bell-shaped dose-response curve (shown in FIG. 6) to the right, increasing the dose required for both agonist and antagonist activities. Receptor binding at site 1 of prolactin is required for both agonist and antagonist activities, and by reducing the attraction between site 1 and receptor, both agonist and antagonist processes require a higher hormone concentration to achieve effects comparable to wild-type ligand. The results of these two types of binding site blockage have been reported in the chemical literature and are generally accepted as the functional results of directly blocking either sites 1 or 2.

Antagonists of the type described in this application can result in a unique response profile in a dose-response experiment (as shown in FIG. 6). Again, such antagonists include those in which neither site 1 nor site 2 is blocked, but communication between site 1 and site 2 is affected such that when the ligand binds to receptor at site 1, site 2 does not become available for binding to receptor as it does in wild-type ligand. The biological response of such an antagonist in dose-response studies is that the agonist phase (the part of the curve where activity is increasing as concentration increases) of the bell-shaped dose-response curve is shifted to the right as compared to the curve obtained with agonist (e.g., prolactin), but the antagonist phase (the part of the curve where activity is decreasing as concentration increases) is not changed. These antagonists result in this type of curve because site 2 is necessary only for the agonist phase of the dose-response curve and uncoupling site 2 function from site 1-induced effects shifts the agonist phase right.

In contrast, the antagonist phase of the dose-response curve is solely mediated by site 1 binding to receptor. If structural changes in the ligand do not influence site 1 function then the antagonist phase is not affected in such assays. These types of assays are used to quickly screen for and identify variants of prolactin that will function as antagonists (see Duda, K. M. and Brooks, C. L., FEBS Letters 449: 120–124 (1999) for details of this assay).

The present strategy is used to identify the inventive antagonists of the invention. Such an antagonist can have the following features:

1) The protein has antagonist activity;
2) The protein has a functional receptor-binding site 1;
3) The protein is not able to bind receptor through site 2;
4) The protein folds properly (i.e., folds as native, un-mutated protein); and
5) The protein has little or no agonist activity.

Throughout the specification, reference is made to peptide and protein hormone variants, in which amino acids are mutated by, for example, deletion or substitution. It should be noted that other modifications are specifically contemplated as well. For example, modifications to change the pharmacokinetic profile of the inventive compounds, or to otherwise modify their physicochemical characteristics, such as through the use of pegylation, lipidation, glycosylation, phosphorylation, or any other chemical (including peptide and nucleic acid) addition, are specifically contemplated. Examples of methods for achieving such modifications are well known to those of ordinary skill in the art.

Treatment

The prolactin antagonists of the invention can be administered using those methods currently used to administer somatotropin, or growth hormone (see *Physicians Desk Reference; Goodman and Gilman's The Pharmacological Basis of Therapeutics, 8th edition* (1990); also see *Remington's Pharmaceutical Sciences*; all of which are specifically incorporated herein by reference)).

The present invention provides methods for treatment of various conditions or methods for prophylaxis of various conditions. One particular use of the prolactin antagonists of the present invention is for therapeutic treatment of cancers whose growth is responsive or dependent on prolactin. Such cancer cells may not proliferate well or do not proliferate at all in the absence of prolactin. Treatment of such cancer subjects with prolactin antagonists is beneficial in that the treatment suppresses or halts proliferation, growth, and/or division of the cancer cells. It should be appreciated that, in some instances, treatment of a subject with a cancer whose growth, proliferation or cell division is not responsive to or dependent on prolactin, with prolactin antagonists may be beneficial.

Another use of the present prolactin antagonists is the therapeutic treatment of cancers whose survival is enhanced or even dependent on the presence of prolactin. Treatment of subjects with such cancers with prolactin antagonists is beneficial in that the treatment causes decreased survival of the cancer cells. Cancer cells so treated may die by one of various processes. One such process is necrosis. Another such process is apoptosis, also called programmed cell death. It should be appreciated that prolactin antagonists may, in some instances, cause decreased survival or death of cancer cells whose survival is not enhanced or dependent upon prolactin.

Another use of the prolactin antagonists is for therapeutic treatment of cancers such that the prolactin antagonists reduce or prevent metastasis of the cancer cells in the body of a subject.

It should be appreciated that these methods are used therapeutically, in the case where a subject has a tumor or cancer that can be treated with prolactin antagonists. The methods can also be used to prevent the formation of a tumor or cancer in individuals likely to form these.

By way of an example of a specific therapeutic formulation, the prolactin variants of this invention are envisioned as being particularly efficacious in the treatment of prolactin-responsive cancers, such as some lymphomas. In these applications, the variant proteins of the invention can be formulated as an injectable pharmaceutically acceptable formulation. The particular therapy to be given a patient will, of course, vary depending on the age, sex, weight, and stage of the disease. A dosage in schedule of up to about 0.1 mg/kg administered 3 times a week, for example, intramuscularly or subcutaneously, is one regimen for the treatment of some forms of lymphoma. These dose ranges may vary, depending on the response of the patient to the treatment, and may be increased or decreased within a range of between about 8 mg/kg to about 40 mg/kg of a pharmaceutical preparation prolactin protein, depending on response of the patient.

By way of another example, a normal adult human weighing about 70 kg, diagnosed as having a prolactinoma (which results in a hyperprolactinemic condition) or a preprolactinoma condition, is treated with a pharmaceutically acceptable preparation of the prolactin variant proteins described herein. Such a treatment can be administered intramuscularly or subcutaneously at a total dose of between about 14 mg/kg to about 35 mg/kg, so as to achieve an expected circulating level of the substituted protein of between about 90 ng/ml to about 200 ng/ml serum in the patient.

Human patients with a prolactinoma, having a condition known as hyperprolactinemia, have been documented as having circulating levels of prolactin as high as 20 μg/ml serum. Based on these levels, the above-identified dose ranges constitute reasonable ranges of the substituted prolactin as a prolactin antagonist in the treatment of this condition in the patient.

The inventive compounds can be orally administered, for example, with an inert diluent or with an edible carrier, or they may be enclosed in a hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations can contain at least 0.1% of the active substituted prolactin protein or peptide compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain one or more of the following pharmaceutically acceptable excipients: a binder, such as gum tragacanth, acacia, cornstarch, or gelatin; dicalcium phosphate; a disintegrating agent, such as corn starch, potato starch, alginic acid and the like; a lubricant, such as magnesium stearate; a sweetening agent, such as sucrose, lactose, or saccharin; and/or a flavoring agent, such as peppermint, oil of wintergreen, or cherry flavoring. Examples of other pharmaceutically acceptable excipients are well known to those of ordinary skill.

When the dosage unit form is a capsule, it may contain, in addition to materials of the above type, a liquid carrier. Various other materials may be present as coatings or otherwise to modify the physical form of the dosage unit. For instance, tablets, pills, or capsules may be coated with shellac, sugar, or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The active compounds can also be administered parenterally or intraperitoneally. Solutions of the active compounds can be prepared in water suitably mixed with a surfactant. Dispersions can also be prepared in glycerol, liquid polyethylene glycols, and mixtures thereof and in oils. Under ordinary conditions of storage and use, these preparations contain a preservative to prevent the growth of microorganisms.

It is also contemplated that the presently described variant prolactin proteins may be formulated as a nasal spray, and used in therapeutically effective doses to treat the various prolactin-related disorders noted herein.

Sterile injectable solutions can be prepared by incorporating the active compounds in the required amount in the appropriate solvent with various of the other ingredients enumerated above, as required, followed by filter sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The inventive prolactin antagonist proteins in compositions are suitable for single administration or in a series of administrations. The administrations can be parenteral, topical, and/or oral administration. Parenteral administration is preferably by intravenous, subcutaneous, intradermal, intraperitoneal, or intramuscular administration. For parenteral administration, the compositions can include prolactin antagonists and a suitable sterile carrier such as water, aqueous buffer, 0.4% saline solution, 0.3% glycine, hyaluronic acid or emulsions of nontoxic nonionic surfactants as is well known in the art. The compositions may further include substances to approximate physiological conditions such a buffering agents and wetting agents such as NaCl, KCl, $CaCl_2$, sodium acetate and sodium lactate. It should be noted that, in addition to administration of prolactin antagonist protein in a pharmaceutically-acceptable composition, DNA or RNA encoding prolactin antagonist proteins may also be administered as a part of such a composition.

Compositions suitable for parenteral administration also may conveniently comprise a sterile aqueous or oleaginous preparation of prolactin antagonist, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulations suitable for oral, subcutaneous, intravenous, intramuscular, etc. administrations can be found in Remington's Pharmaceutical Sciences, Mack Publishing Co., Easton, Pa. The pharmaceutical compositions may conveniently be presented in unit dosage form and may be prepared by any of the methods well-known in the art of pharmacy.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Methods of Treatment

A therapeutically or prophylactically effective dose of the prolactin antagonist protein composition is administered to the individual. The composition can be administered as a single dose, or a series of dosages over a period of days, weeks, or even months. As used herein, an effective therapeutic dose is a dose that inhibits growth of a tumor, or even causes tumor regression. Such a dose also may inhibit or prevent metastasis of a tumor. Herein, an effective prophylactic dose is a dose that prevents or slows the formation of a tumor. In the case of non-solid tumors, effective therapeutic doses can result in a movement toward normal blood cell counts, and/or remission of the disease.

The pharmaceutical compositions, generally speaking, can be administered using any mode that is medically acceptable, meaning any mode that produces the desired anti-tumor activity without causing clinically unacceptable adverse effects. Such modes of administration include parenteral routes (e.g., intravenous, intra-arterial, subcutaneous, intramuscular, mucosal, or infusion), but may also include oral, rectal, topical, nasal, or intradermal routes. Other delivery systems can include time-release, delayed release, or sustained release delivery systems. Such systems can avoid repeated administrations, increasing convenience to the subject and the physician. Many types of delivery systems are available and known to those of ordinary skill in the art.

Other routes of administration include injection of the prolactin antagonist composition directly into the tumor (i.e., intratumoral administration). Other methods include injection of the prolactin antagonist intravenously, intraperitoneally, intramuscularly, subcutaneously, or intracerebrally. Other methods of administering can be used.

The above methods for cancer treatment (i.e., administration of a prolactin antagonist) may be combined together and/or may be combined with other known methods for treating a particular cancer. Such methods may include chemotherapy, surgery, radiotherapy, photodynamic therapy, gene therapy, antisense therapy, enzyme prodrug therapy, immunotherapy, fusion toxin therapy, antiangiogenic therapy, or any combination of these therapies.

In the administration of the prolactin antagonists as described above, drug delivery devices such as infusion pumps may be utilized, or the composition may be administered in the form a denatured pellet, or in a hydrogel, or nano or microparticles.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Further details of the invention can be found in the following examples, which further define the scope of the invention.

Example 1

Mutant Human Prolactins have Tertiary Structures Similar to Wild-Type Protein A study was designed to discriminate between two models of hormone mechanics: an induced-fit model (as described in this application), or a model with constitutively-active and independent-sites (the model currently described in the literature; not an induced-fit model). The experimental hypothesis was that if the first or second site was chemically altered to reduce or eliminate function, then it should still be possible to discern binding at the other site (the independent-binding site model). If data could not support the independent-binding site model, then the null hypothesis of an induced-fit model would be accepted.

The approach was to prepare three human prolactins by recombinant DNA technology, site-directed mutagenesis, and expression of the recombinant proteins in *E. coli*. One of the prolactin mutants had a mutation within site 1 (lysine 181 mutated to cysteine; K181 C), one had a mutation within site 2 (glycine 129 mutated to cysteine; G129C), the third had a mutation at a site irrelevant to either site 1 or 2 binding (methionine 158 mutated to cysteine; M158C).

The in vitro mutagenesis was performed by the method of Kunkel (T. A. Kunkel, K. Bebenek and J. McClary, *Methods in Enzymol.* 204:125–139 (1991)). Primers were designed to produce the desired mutations and either add or delete a translationally silent restriction endonuclease site to allow rapid selection of potential mutants. The DNA coding for human prolactin from clones identified by restriction digests were completely sequenced to confirm the presence of the desired mutation(s). These techniques are well known in the art.

Purified phagemids encoding the prolactins were transformed into BL21 (DE3) *E. coli* cells and expressed and purified as previously described (F. C. Peterson and C. L. Brooks, *J. Biol. Chem.* 272:21444–21448 (1997); F. C. Peterson, P. J. Anderson, L. J. Berliner, and C. L. Brooks, *Protein Expression and Purification* 15:16–23 (1999)). Phagemid pT7—7 was used as has been described (K. M. Duda and C. L. Brooks, *FEBS Letters* 449:120–124 (1999)). Proteins were evaluated for size and purity by 15% SDS-PAGE under non-reducing or reducing conditions. Absorption, fluorescence and far UV circular dichroism spectra were collected at 20° C. in 10 mM Tris pH 8.2, 150 mM NaCl.

Figure 7:
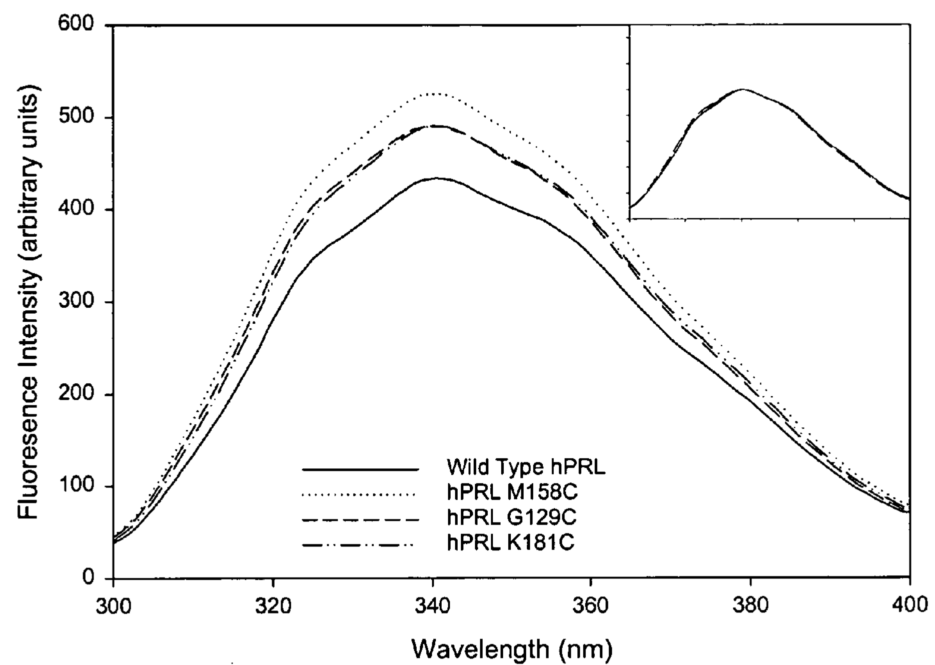
FIG. 7 shows emission fluorescence spectra of recombinant mutant and wild-type human prolactins. The raw data are shown in the main graph. Data normalized to a 340 nm reading are shown in the inset graph and allow a comparison of the shapes of the signals that form the fluorescence curve. The fluorescence spectrum provides information regarding the folding and environment of the amino acids in the hydrophobic core of the protein. The data for each mutant protein closely overlay that of wild-type human prolactin, indicating that the mutant proteins fold nearly identically to wild-type human prolactin.
Figure 8:
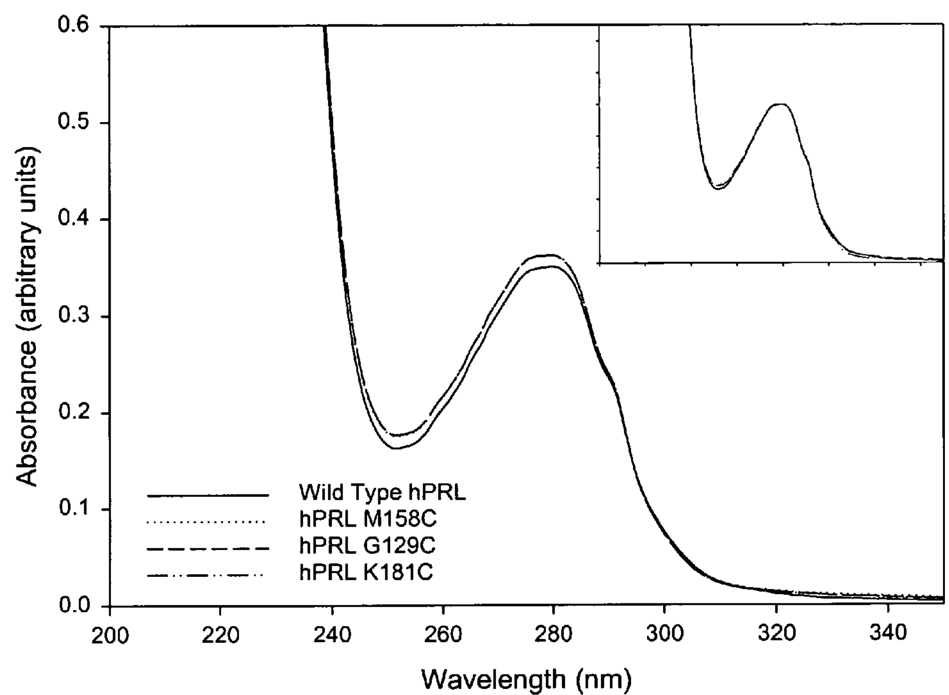
FIG. 8 shows absorption spectra of recombinant mutant and wild-type human prolactins. The raw data are shown in the main graph. Data normalized to a 280 nm reading are shown in the inset graph to facilitate comparison of the relationship of the absorption curves. Absorption spectra provide information on the several hydrophobic residues including phenylalanine, tyrosine and tryptophan in the 280 nm region and on the spatial geometry of disulfide bonds in the 250 region. The data show that these selected mutations produce a protein that is indistinguishable from wild-type human prolactin.
Figure 9:
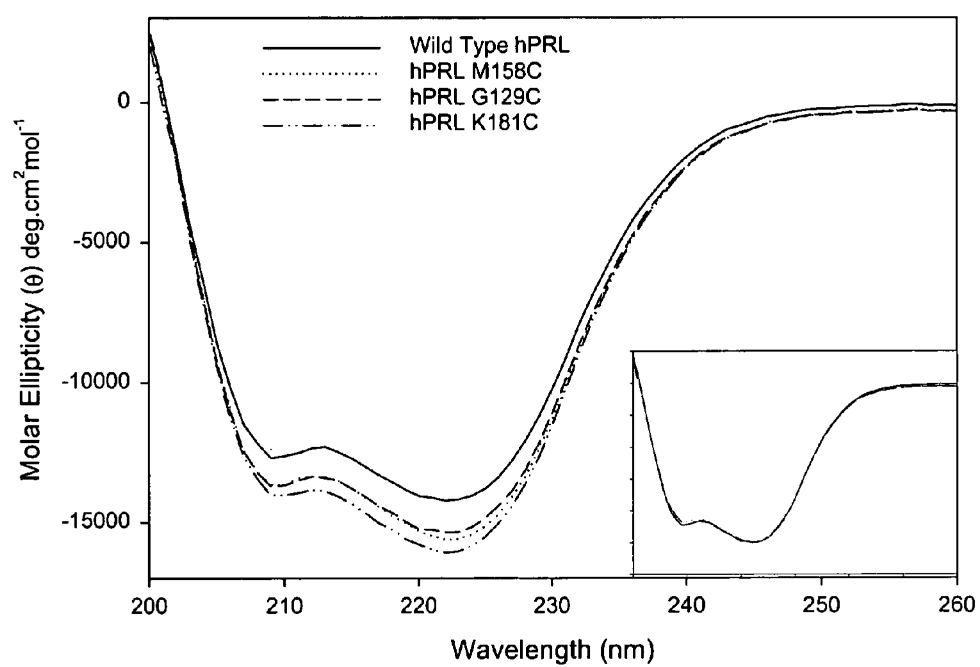
FIG. 9 shows circular dichroism spectra of recombinant mutant and wild-type human prolactins. The raw data are shown in the main graph. Data normalized to a 222 nm reading are shown in the inset graph to allow comparison of spectral shapes. Circular dichroism spectra in the in the far UV region provide information-regarding the secondary folding structure of the protein. The spectra closely overlay indicating that the mutant proteins fold nearly identically to wild-type human prolactin.

The proteins were characterized for their folded structural properties by fluorescence spectroscopy (FIG. 7), ultraviolet spectroscopy (FIG. 8), and circular dichroism (FIG. 9). Absorption spectra for the different prolactins overlay each other (FIG. 8) indicating that the tertiary structures of these proteins are very similar. Fluorescence emission spectra of the recombinant human prolactins also overlaid each other (FIG. 7), indicating similar structures of the proteins as determined by the molecular environment surrounding the endogenous fluorochromic amino acids. Likewise, circular dichroism spectra of the recombinant human prolactins overlaid each other (FIG. 9), indicating that the protein had similar contents of secondary structures (α-helices).

The results for each protein mutant were indistinguishable from the parent protein, indicating that the proteins had been successfully folded to the wild-type structure. Thus, experimental results could be attributed to the specific structural changes produced by mutagenesis and their associated functional changes in the mechanics of the various proteins rather than anomalous folding of the recombinant protein.

Dose-response studies using cells that respond to prolactin by increased growth showed M158C human prolactin to have full biological activity, while K181C and G129C human prolactins lost some biological activity. This was expected because modest structural changes were being made within sites 1 and 2, respectively.

Example 2

Biological Functioning of Prolactin Mutant Proteins Show that Lactogenic Receptor Binding at Site 2 Requires Binding at Site 1 (Demonstrates an Induced-Fit Model)

Binding experiments were monitored by surface plasmon resonance on a BIACORE™ 3000 instrument. The design of these instruments requires one of the binding components to be covalently attached to a microfluidic optical chip surface. This approach was taken to allow multiple extracellular domains of the human prolactin receptor to bind the fixed ligand. Subsequently, the extracellular domain of the human lactogenic receptor is flowed across the chip surface at a prescribed concentration and for a defined duration. Binding of human prolactin and the receptor that occurs on the protein-containing side of the microfluidic optical chip was observed by an optical bench located on the back of the chip surface. In the experiments, we covalently attached the human prolactins to the chip surface through a dextran polymer linked by a thiol to form a disulfide bond with the cysteines placed at residues 129,158, or 181. By this chemistry, a large dextran polymer was anchored within either site 1 or site 2 rendering them non-functional. Coupling by a functionally irrelevant site (M158C) produced an anchored hormone with two functional receptor-binding sites. The relative amounts of the lactogenic receptor bound to the prolactins fixed to the chip surface and the chronology of the binding event were followed on the Y-axis and X-axis, respectively.

Experiments were then performed in studies that measured the maximal binding of lactogenic receptor (the extracellular domain of the prolactin receptor prepared by recombinant DNA technology). The various prolactins were bound with high concentrations (100 μM) of extracellular domain of the human prolactin receptor. In these experiments, maximal binding was reached within the first 50 to 100 seconds, allowing equilibrium to be achieved and the relative amounts of receptor binding to each hormone variant to be observed at times up to approximately 250 seconds. The relative amounts of lactogenic receptor binding can be seen on the Y-axis of FIG. 10 (top frame). Human prolactin is capable of binding two receptor proteins when coupled to the chip surface at position 158. When prolactin was coupled to the chip surface at position 129, site 2 was blocked by the coupling chemistry and the amount of receptor bound by prolactin was cut in half (49.8%) indicating that site 1 was fully capable of binding receptor and could function independently of site 2. When human prolactin was coupled to the chip surface at position 181, blocking site 1, little binding was observed (approximately 5%). This demonstrates that when receptor binding at site 1 was blocked, receptor binding at site 2 did not occur. Thus, site 2 binding of receptor was dependent on completion of receptor binding at site 1. This data shows that site 2 binding is dependent on site 1 binding; therefore, the hypothesis of independent receptor function must be dismissed. Further, the data strongly support our induced-fit model where binding at site 1 induces a conformation change in human prolactin that results in the rearrangement of the atoms that compose site 2 creating the second functional receptor binding site.

The dissociation of receptor from the various human prolactins (viewed in FIG. 10, top frame, as the time points beyond approximately 250 seconds) also demonstrates characteristics of an induced-fit model. The prolactin coupled to the chip surface through residue 158 show a two-phase dissociation, one rapid and one considerably slower. Both dissociation processes are apparent because the high receptor concentrations have saturated all binding sites of human prolactin. The rapid dissociation phase represents dissociation of receptor from site 2 of human prolactin, while the slower phase represents dissociation of receptor from site 1. When human prolactin is coupled to the chip surface via site 2 (by residue 129), only the slow dissociation process of site 1 is observed. Finally, when site 1 is blocked by the coupling reaction, insufficient receptor is bound at site 2 to determine that a significant dissociation process occurs.

These experiments confirm our hypothesis that sites 1 and 2 are functionally coupled. This discovery provides a new target for the development of an entirely new class of human prolactin antagonists and sets the paradigm for the development of additional antagonists in other members of this protein family that use an induced-fit coupling of their receptor binding sites.

Example 3

Kinetic Binding Experiments

Time-dependent binding kinetic provides a second set of data that accurately describe both the rates and strength of prolactin-receptor binding. Using the same set of human prolactins bound to the chip (M158C, G129C, and K181C) as described above, we undertook kinetic studies with much lower concentrations of receptor being flowed over the chip surface. One study used several concentrations between 50 and 800 nM of the extracellular domain of the human prolactin receptor and compared the shapes of the receptor binding curves to human prolactins coupled to the chip surface at residues 129, 158, or 181. In FIG. 11, the shapes of these sets of three binding curves can be compared; the kinetics of each binding are substantively different.

Coupling human prolactin to the chip surface at position 158 shows a complex curve, where site 1 binding dominates the early times in the experiments, but as site 1 binding activates site 2 binding continues to increase until the end of the association phase. The dissociation is largely a single slow phase reflecting receptor dissociation from site 1. In this case, site 2 receptor binding is small due to the limited time and low receptor concentration used during the association phase. Thus, the rapid dissociation of receptor from site 2 is lost in the dominant site 1 dissociation signal. Blocking site 2 by coupling human prolactin to the chip surface by residue 129 produces a single rapid binding component that approaches equilibrium and provides less binding than that observed with 158C-coupled human proalctin. These receptors dissociate slowly as a single class. These are the kinetics of site 1 association and dissociation. Finally, blocking site 1 by coupling human prolactin to the chip surface via residue 181 essentially eliminates receptor binding to either site 1 or site 2. This indicates that site 2 has a greatly reduced binding capacity when site 1 is not occupied by a lactogenic receptor.

These comparative kinetic studies also fail to support the independent function of receptor binding sites 1 and 2 of human prolactin. Similar to the equilibrium studies, the data are consistent with an induced-fit model where receptor binding at site 1 is required for receptor binding to occur at site 2 of human prolactin.

Example 4

Measurement of the Kinetic Rate Constants for Human Prolactins

Knowledge of an induced-fit mechanism of human prolactin binding lactogenic receptors allows performance of more complex kinetic experiments and analysis of results based upon a valid model. We have undertaken these experiments by surface plasmon resonance technology fixing human prolactin to the chip surface by coupling within site 1 (by residue 181), site 2 (by residue 129), or at a position distal to either binding site (by residue 158). The extracellular domain of the human lactogenic receptor was flowed across the prolactin-linked chip surface at various concentrations and the binding kinetics followed by the optical bench. Human lactogenic receptor (extracellular domain) concentrations varied between 50 nM and 800 nM. The association and dissociation phases of the binding curves were fit with an induced-fit model for M158C human prolactin, where both sites were available. A single receptor model was used for G129C human prolactin, where site 2 was blocked by the chemistry employed to couple the protein to the chip surface. No kinetic rates could be calculated from the human prolactin coupled to the chip surface via site 1.

FIG. 11 is a representative study showing the raw data for lactogenic receptor binding to each of these three human prolactins. Increasing concentrations of receptor produced a more rapid binding providing high quality data for simultaneous mathematical fitting to the appropriate kinetic equations. Dissociation data at these receptor concentrations was dominated by the slow dissociation of receptor from site 1, therefore calculated rate constants for site 2 contains greater ambiguity. The kinetic rate constants and the derived equilibrium constants were calculated (Table 1).

Rate constants were calculated from the association and dissociation curves, respectively, with concentrations of the extracellular domain of the human lactogenic receptor (50, 80, 100, 200, 500 and 800 nM).

TABLE 1

| Association and Dissociation Kinetics of Human Prolactins | | | | | | |
|---|---|---|---|---|---|---|
| | Site 1 | | | Site 2 | | |
| Mutant Prolactin | $k_{a1}$ ($M^{-1}s^{-1}$) $\times 10^3$ | $k_{d1}$ ($s^{-1}$) $\times 10^{-3}$ | $K_{D1}$ (nM) | $k_{a2}$ ($M^{-1}s^{-1}$) $\times 10^3$ | $k_{d2}$ ($s^{-1}$) $\times 10^{-3}$ | $K_{D2}$ (nM) |
| M158C | 14.3 ± 2.2 | 1.57 ± 0.37 | 109.4 | 2.56 ± 0.46 | 0.39 ± 0.39 | 153.1 |
| G129R | 19.6 ± 0.9 | 1.19 ± 0.11 | 60.5 | — | — | — |

The residuals and Chi-square values for this data set are sufficiently small to indicate that the models (induced-fit binding for M158C human prolactin or single-site binding for G129R human prolactin) describe the data well.

The association rate constant and dissociation rate constant for site 1 are similar for M158C and G129C human prolactins. This shows that binding at site 1 is not highly influenced by a functional or blocked site 2. In other words, site 1 functions independently of site 2. The forward rate constant of site 1 is 5 fold higher than that for site 2. This is consistent with the observation that in G129R human prolactin binding at site 1 approaches equilibrium by 250 seconds when incubated with 800 nM receptor, while in M158C human prolactin under the same conditions equilibrium is not achieved.

The primary structural difference between M158C and K181C human prolactins is that both receptor-binding sites are functional in M158C and only site 2 is available in K181C human prolactin. In equilibrium experiments, approximately 95% of site 2 binding is lost, confirming the dependence of site 2 binding on prior occupancy of site 1. This information is consistent with an induced-fit model where human prolactin is in equilibrium between a site 2 active and site 2 inactive conformations. In the absence of site 1 binding the conformational equilibrium of human prolactin strongly favors the form where site 2 is inactive. In contrast, when site 1 is bound by a lactogenic receptor the conformational equilibrium strongly favors the site 2 active form of human prolactin.

Based on the consistent results from both equilibrium and kinetic experiments the independence of receptor binding sites of human prolactin is not supported. Rather, the data support an induced-fit model where receptor binding at site 1 of human prolactin is required prior to receptor binding at site 2. These studies are the first to demonstrate an induced-fit mechanism for human prolactin binding to the lactogenic receptor.

A direct implication of the induced-fit model is that sites 1 and 2 communicate. Such communication must rely on the physical features of the molecule; specifically the mechanism by which amino acid residues propagate a communication between sites 1 and 2. Knowledge of the protein structures that participate in the mechanics by which the induced-fit mechanism propagates a conformation change from site 1 to site 2 is valuable information in that it allows the rationale design of a new class of super agonists and antagonists of human prolactin. Super agonists and antagonists of human prolactin may have application as pharmaceutical agents.

Example 5

Identification of Amino Acid Residues that Propagate the Receptor Binding-Induced Conformation Change We reasoned that specific structural elements of human prolactin participate in the propagation of a site 1 binding-induced conformation change. If these structural features were changed by mutating specific amino acids then the ability to propagate a conformation change to site 2 will be diminished and the activity at site 2 should be reduced. We have prepared several mutant human prolactins and growth hormones using this mutational approach and tested them for a functional site 2 by assessing their activity in a prolactin bioassay (see Duda and Brooks *FEBS Letters* 449:120–124 (1999) for experimental methods).

Studies of Lactogenic Activity of Human Prolactin

Studies have been preformed with human prolactin to identify specific structural features of the protein that are distal from sites 1 and 2, but are required for the binding, dimerization and activation of prolactin receptors. In human prolactin we have identified residues in mini-helix 1 (residues 41 through 57), helix 4 (residues 160 through 173), and the residues between 94 through 110. Mutations have changed the nature of the residue present in wild-type human prolactin and are effective at perturbing the function of the atoms in the location without disturbing the global structure of the protein. Thus, if mutation of an amino acid reduces the biological activity in the manor described by K. M. Duda and C. L. Brooks (*FEBS Letters* 449, 120–124 (1999)), then that residue participates in the propagation of a site 1 receptor binding-induced conformation change in human prolactin.

Variant prolactin molecules (F50E, L95E, L98E, L165E, Y169E, L171E, and H173E, among others) were made using in vitro mutagenesis performed by the method of Kunkel as described in Example 1. The variant proteins were then purified as described in Example 1.

Wild-type and variant prolactins were used to stimulate growth of FDC-P1 cells that were transfected with the human prolactin receptor. FDC-P1 cells containing the prolactin receptor were obtained from Genentech Incorporated, South San Francisco, Calif. Cells were maintained win RPMI 1640 containing 10 μM 2-mercaptoethanol, 1 nM wild-type human growth hormone, and 10% fetal calf serum. Log phase cells were collected and washed three times with non-supplemented RPMI 1640. Washed cells were suspended in media devoid of wild-type growth hormone and phenol red but supplemented with 10% gelding horse serum. Cells were maintained under these conditions for 24 h immediately prior to the assay. Prolactin and variant prolactins were diluted with phenol red-free media to the desired concentrations and added to cells grown in 96 well plates in triplicate wells. Each well contained 15,000 FDC-P1 cells in a total volume of 100 μl. Plates were gently agitated and then incubated at 37° C. in a 5% $CO_2$/95% air atmosphere for 48 hours.

Hormone-induced proliferation of the cells was assessed by a vital dye method with the addition of 10 μl of Alamar blue (Accumed International, West Lake, Ohio) per well, followed by a 4-h incubation. The oxidation-reduction of Alamar blue was evaluated at 570 and 600 nm. These values were used to calculate the percentage reduction of the dye, which is highly correlated with the viable cell number ($r^2$>0.99). The values obtained from dose-response studies were used to calculate $ED_{50}$s for the agonist phases by a four parameter-fit method (Munson P. and Rodbard D., *Anal. Biochem.* 107:220–239 (1980)). $ID_{50}$s for the antagonist phases were estimated from plots of the dose-response curves. In instances where the antagonist phase of the dose-response curve reached the x-axis, values determined by the four-parameter fit method and graphical estimation were similar.

The wild-type prolactin concentration required to elicit a half maximal agonist response ($ED_{50}$) was 0.72 nM. In contrast, the concentrations of F50E, L95E, L98E, L165E, Y169E, L171E, and H173E variants to elicit the same response was approximately 5-, 8-, 88-, 41-, 90-, 8- and 1,569-fold higher, respectively (Table 2). Other residues tested had fold changes in their $ED_{50}$s between 0.6 and 1.0. Thus, the amino acids that participate in this reaction were easily identified among those tested. The mutated residues that fit the criteria to be identified as members of the motif that propagates the site 1 binding-induced conformation change are found in the regions that were previously indicated, including the residues between 41 through 57 (the mini-helix 1 region), 94–110 (the residues between the proline in helix 2 and the beginning of helix 3), and 160 through 173 (residues in the N-terminal portion of helix 4). Additional residues in the mini-helix 1 region have been tested and also suggest that they may be included in the propagation motif (residues 45 through 54, except T52).

TABLE 2

Lactogenic Activities of Human Prolactins

| | FDC-P1 lactogenic assay | |
|---|---|---|
| | $ED_{50}$ (nM) | Relative fold loss of activity |
| WT hPRL | 0.72 | 1.0 |
| F50E | 1.0* | 5.0 |
| ΔF50 | 0.03** | 2.7 |
| L95E | 5.6 | 7.8 |
| L98E | 63.1 | 87.7 |
| L165E | 29.5 | 41.0 |
| Y169E | 64.8 | 90.0 |
| L171E | 5.7 | 8.0 |
| H173E | 1130 | 1569 |

*Establishment of the agonist portion of the dose-response curve was incomplete, but the agonist phase was right-shifted.
**This assay was performed separately from the other data displayed in this table. WT-hPRL $ED_{50}$ was 0.2 nM.

When the residues identified by these mutagenic studies are projected onto the nuclear magnetic resonance structure of human prolactin (FIG. 13) they form a hydrophobic core that runs from site 1 to site 2. The residues that constitute the motif that propagates the site 1 binding-induced conformation change that functionally couples sites 1 and 2 are similar but not identical for both human prolactin and growth hormone (see following section). Thus, it appears that similar mechanisms are present in both lactogenic hormones.

Since mutations in the above variants are not within site 1 or site 2, the mutations reduce the biological activity of the variants by disrupting the propagation of a site 1 receptor binding induced conformation change in prolactin. Therefore, these data indicate that a cluster of hydrophobic residues have been identified that articulate between and functionally couple site 1 to site 2. These and other amino acid residues are the physical manifestations of the mechanism that is required for the conformation change and the appropriate function of human prolactin.

In addition to the data shown above, complete dose-response curves, as shown in FIG. 6, were obtained for both wild-type prolactin and the variants described above. For each of the variants, the data show that the agonist-phase of the curve was right-shifted as compared to the curve for wild-type prolactin (e.g., see the increased $ED_{50}$s for the variants in Table 2 above), while the curve for the antagonist phase for the three variants was unchanged as compared to the antagonist curve for wild-type prolactin. This observation indicates that the structural changes provided by mutation only changed the function of site 2 (the agonist phase of the dose-response curve is dependent on both site 1 and site 2 function). The same structural changes did not affect site 1 (the unchanged antagonist phase of the dose-response curve is dependent only on site 1 function). Therefore, each of these mutations identifies an amino acid in the structure human prolactin that is required for the communication between sites 1 and 2.

Based on these studies of the mechanism, we have described a mechanism by which the conformation change is propagated. When site 1 of human prolactin or growth hormone binds a prolactin receptor the receptor is sufficiently large to cover a sizable surface of the ligand. Binding at site 1 is of sufficient strength at some locations in this binding surface that it will pull the receptor into position. As this docking of hormone and receptor occurs, some structural features of the binding interface may be changed by the close proximity of the molecule being bound. Crystallographic evidence for such structural changes can be observed if one compares the structures of human growth hormone bound to the or free from the human prolactin receptor (FIG. 14; Protein Data Base, http://www.rcsb.org/pdb/, Protein Data Base # 1HGU, Chantalat, L., Jones, N., Korber, F., Navaza, J. and Pavlovsky, A. G. Protein and *Peptide Letters* 2, 333–340 (1995); and Protein Data Base # 1BP3, Somers, W., Ultsch, M., de Vos, A. M. and Kossiakoff, A. A. Nature 372, 478–481 (1994)).

When we compare the positions of the motif residues in receptor bound and unbound human growth hormone we observe that the prolactin receptor bound to site 1 covers the mini-helix-1 region. In doing so, the motif residue F44 is rotated from being solvent-exposed to be tucked between Y160 and Y164. The placement of F44 perturbs the residues in the N-terminus of helix 4 causing a small unwinding of the helix that rotates L163 toward the region connecting helices 2 and 3. Examination of the structures of this section reveals that those residues beyond P90 to the beginning of helix 3 are non-helical when the ligand is not bound to the prolactin receptor, but form a 10 amino acid extension of helix 2 when site 1 is receptor bound. The extension of helix 2 orders the residues tethered to the N-terminus of helix 3 and restricts the position of helix 3 relative to the body of the protein. In this manner, we believe that helix 3 is brought into a more stable position relative to helix 1. This structure is now able to bind a second prolactin receptor at site 2 (located in the groove between helices 1 and 3). In our mutagenic studies with both human growth hormone (see next section) and the human prolactin receptor we have demonstrated that replacement of amino acids that constitute this motif diminish the functional coupling of the two receptor binding sites.

Less structural information is available for human prolactin, but many of the same features that are present in human prolactin are also found in the motif found in human growth hormone (FIG. 13). Most interesting is that in the structure of prolactin free from receptor, F50 located in mini-helix 1 is rotated away from the hydrophobic cluster located in the residues in the N-terminal of helix 4, this is highly homologous to the structures of human growth hormone.

Studies of Lactogenic Activities of Human Growth Hormone

The results for our work with the lactogenic activity human growth hormone has recently been published (Duda, K. M. and Brooks, C. L., *Journal of Biological Chemistry* 278, 22734–22739 (2003)) and reveals a set of largely hydrophobic articulating residues that lay between sites 1 and 2. These amino acids include F44, L93, Y160, L163 and Y164 (Table 3). These amino acids are located in mini-helix 1 and helices 2 and 4. These regions are homologous to regions in human prolactin that we have proposed as the principle structural features that propagate the site 1 binding-induced conformation change. Equally relevant is that the mutations that reduce the activity of human growth hormone to stimulate the prolactin receptor do not influence its ability to stimulate the growth hormone receptor. Thus, the mechanism of human growth hormone required to bind and dimerize prolactin receptors is very specific, in that these mutations do not alter the hormone's ability to interact with the growth hormone receptor.

TABLE 3

Lactogenic and Somatotrophic Activities of Recombinant hGHs

| | FDC-P1 lactogenic assay | | FDC-P1 somatotrophic assay | |
|---|---|---|---|---|
| | $ED_{50}$ (nM) | Relative fold loss of activity | $ED_{50}$ (nM) | Relative fold loss of activity |
| WT hGH | 1.76 | 1.00 | 0.0712 | 1.00 |
| F44E | 147 | 83.8 | 0.576 | 8.09 |
| L93E | 8.22 | 4.66 | 0.234 | 3.29 |
| Y160E | 15.8 | 9.00 | 0.186 | 2.62 |
| L163E | *** | *** | *** | *** |
| L163A | 6.14 | 3.49 | 0.130 | 1.83 |
| L163F | 13.8 | 9.00 | 0.235 | 3.30 |
| Y164E | 152.0 | 86.5 | 0.151 | 2.12 |

***$ED_{50}$s could not be calculated from the results of the biological assay due to severe disturbance of the protein structure by the L163E mutation. To determine if this residue was a member of this motif more subtle mutations (replacing leucine with alanine or phenylalanine) were performed.

Example 6

Human Prolactin Undergoes a Conformation Change When Binding the Lactogenic Receptor One of the features of our mechanism is that binding of prolactin receptor at site 1 of human prolactin induces a conformation change. We have undertaken fluorescence resonance energy transfer (FRET) studies to document the presence of a binding-induced conformation change. In these studies, the FRET signal is inversely proportional to the sixth power of the distance between two fluorochromes. We have chosen to use the two tryptophans of human prolactin as the first fluorochromes. They are excited by light at 295 nm and by a resonance mechanism can transfer the energy from the absorbed light to certain secondary fluorochromes (coumarin in our system). This reduces the fluorescence emission from the primary fluorochrome. The secondary fluorochrome emits the energy captured by resonance transfer as light. Changes in the distance between the two fluorochromes that are induced by a site 1 binding-induced conformation change will increase the coumarin emission as the distances between the two fluorochromes are decreased.

We have added coumarin to the M158C mutant of human prolactin by a maleimide covalent coupling to form a thioether with the free cysteine at position 158. We have previously shown that chemical modification at this site does not inhibit folding or receptor binding. We incubated increasing concentrations of prolactin receptor with the coumarin-labeled human prolactin, excited the protein mixture at 295 nm and have recorded the emission spectra between 300 and 570 nm (FIG. 14). Tryptophan's emission maximum is around 350 nm while that of coumarin is around 469 nm.

We observe that the coumarin emission (at 469 nm) increases in proportion to the concentration of receptor added to 1 μM of prolactin. The data indicate that that the average distance between the two tryptophans and the coumarin is reduced by the binding of prolactin receptor by human prolactin. This demonstrates that the binding of prolactin receptor by human prolactin induces a change of conformation of human prolactin.

We must note that the prolactin receptor also contains several tryptophan residues and these may provide a small contribution to the FRET signal. We have measured the distances between conserved tryptophans and the site where the coumarin would be attached on the hormone using the crystallographic structures of human prolactin (Protein Data Base # 1N9D, Keeler, C., Dannies, P. S., and Hodsdon, M. E., *Journal of Molecular Biology* 328: 1105–1121 (2003)), ovine placental lactogen bound to two rat prolactin receptors (Protein Data Base # 1F6F, Elkins, P. A., Christinger, H. W., Sandowski, Y., Sakal, E., Gertler, A., de Vos, A. M., and Kossiakoff, A. A., *Nature Structural Biology* 7:808–815 (2000)), and human growth hormone bound to one human prolactin receptor (Protein Data Base # 1BP3, Somers, W., Ultsch, M. H., de Vos, A. M., and Kossiakoff, A. A., *Nature* 372:478–481 (1994)). Our measurements show that the tryptophans of the prolactin are at most 12 Å, while the closest tryptophan of the receptor is greater than 24 Å. Since the efficiency of resonance energy transfer falls as the inverse of the $6^{th}$ power of the distance, it is unlikely that a substantive portion of the 469 nM FRET signal is a result of receptor proximity to the coumarin-labeled human prolactin. Our calculations show that approximately 1,% of the FRET signal could be accounted for by receptor proximity. The remainder would be produced from the interactions of the tryptophans and coumarin found in the human prolactin. Note that the increasing fluorescence at approximately 350 nm is dominated by that of the added receptor that swamps out the loss of tryptophan fluorescence from the ligand.

A second caution in these studies is that the maleimide coupling of coumarin is very specific for cysteine residues. There are 6 cysteines in wild-type human prolactin that form three disulfide bonds when the protein is correctly folded. These disulfide bonds should not provide free cysteines for coumarin coupling unless they are reduced. Control experiments using wild-type human prolactin also demonstrate a smaller portion of coumarin coupling, thus the possibility exists that not all coumarins are at linked at position 158.

Example 7

Preparation and Characterization of a New Class of Human Prolactin Antagonists

Based on our identification of specific amino acids that are required to propagate a site 1 binding-induced conformation change to site 2, we sought to identify a modification of the structure of human prolactin that would function as a potent antagonist for human prolactin. In earlier work with human growth hormone, we noted that removal of residues similar to those identified in human prolactin would reduce the activity in NB-2 prolactin-dependent rat cells. We noted that these studies had removed a section of amino acids that included some that were identified in the motif that we had identified as required for the propagation of a site 1 binding-induced conformation change. One of these was a human prolactin where we had removed amino acids 41–52, creating a prolactin mutant called Δ41–52 human prolactin. In this protein, a section of the mini-helix 1 region was removed.

Based on some of the studies we had completed, we reasoned that Δ41–52 human prolactin might not be just a protein that lacked prolactin activity, but it might be a molecule that could function as a prolactin antagonist. We realized from our earlier work that Δ41–52 human prolactin had little remaining activity, but it was unclear if it would still bind prolactin receptors at site 1.

We prepared this protein and characterized it to determine if it would be an example of a new class of prolactin antagonists (antagonists that would suppress site 2 binding by functionally uncoupling sites 1 and 2, rather than by sterically blocking site 2). Δ41–52 human prolactin was prepared in good yields and had a nucleic acid sequence that would be translated to the desired protein. Δ41–52 human prolactin could be successfully be retrieved from the expressing bacteria, folded, and purified by ion exchange chromatography, as is common with both wild-type and mutant prolactins. The purified protein displayed spectroscopic properties similar to those of wild-type human prolactin, indicating that the fold was similar to that of the wild-type protein in terms of disulfide bond formation, hydrophobic packing and secondary structure. Δ41–52 human prolactin appears to be more stable than wild-type human prolactin to thermal denaturation; this is a desirable property for a protein that may serve a pharmaceutical role. Initial studies in human FDC-P1 cells that were transfected with the human prolactin receptor showed a significant reduction in agonist activity and a reduced number of cells or a reduced viability of these cells. These initial studies suggested that Δ41–52 human prolactin might be a potent antagonist for the action of human prolactin.

Example 8

Morphological Changes Indicating the Induction of Cell Death by Δ41–52 Human Prolactin A human prolactin that differs from wild-type in that amino acids 41 through 52 have been deleted (Δ41–52) was made (see FIG. 5) using recombinant DNA techniques well known in the art. Similar results to those obtained with the variants described in Example 5 have been obtained with the Δ41–52 variant of human prolactin, indicating it also is an antagonist of the type described above. This variant was tested for its effects on human breast cancer cells as described below. T47D cells were derived from human breast tumors and have been in continuous culture for an extended period of time. T47D cells have lactogenic receptors and produce human prolactin (the elements of an autocrine system). Thus, prolactin may influence the growth and/or survival of the cells. The presence of the components of a prolactin autocrine system are common to most human breast tumors. Thus, the effect of human prolactin antagonists on growth and survival of these tumor cells is relevant to the nature of many human tumors and the efficacy of human prolactin antagonists as therapeutic pharmaceuticals.

T47D human breast cancer cells (a continuous line of cells derived from a human breast tumor) were grown to approximately 70% confluence on chambered glass microscope slides. Cells were starved for 24 hours in medium containing 1% (by volume) charcoal-stripped fetal calf serum. After starvation, cells were treated as follows for 48 hours with either wild-type human prolactin (0.3 nM) or Δ41–52 human prolactin (500 nM) contained in media with 1% charcoal-stripped serum. After the 48 hour treatment period, cells were stained with Oil Red O and H and E. The following were observed (FIG. 15):

Wild-type human prolactin-treated T47D human breast cancer cells—Throughout the treatment period, these cells retained a normal cellular and nuclear morphology. Cells were plump and spindle-shaped as is typical for breast cancer cells treated with prolactin or growth hormone. Cells remained in close contact with one another. A few detached cells were noted (considered to be within normal limits). Oil Red O staining varied from minimal to moderate with some cells exhibiting little to no lipid staining and other cells exhibiting moderate numbers of stained lipid vacuoles dispersed throughout the cytoplasm. In a few cells, the lipid vacuoles showed a slight peri-nuclear propensity.

Δ41–52 human prolactin-treated T47D human breast cancer cells—After 24 hours of treatment there were numerous detached cells and by 48 hours, 45–55% of cells had detached from the surface of the culture plate. The remaining cells showed a marked loss of contact between adjacent cell borders. The periphery of the cytoplasm of individual cells appeared irregular/undulating and many cells had pseudopod-like cytoplasmic extensions. Some of these cells had small clear punctuate cytoplasmic lesions. There were numerous cells exhibiting marked cytoplasmic and nuclear swelling and often fragmentation of the nucleus. A few cells had a significant amount of positive Oil Red O staining, but the majority of cells exhibited only mild to moderate lipid vacuole staining. Lipid vacuoles were usually dispersed throughout the cytoplasm, but in some cells the lipid vacuoles appear to be positioned eccentrically in relation to the nucleus, sometimes surrounding a peri-nuclear clear space.

FIG. 15 shows photomicrographs of T47D human breast cancer cells that have been treated with either wild-type or Δ41–52 human prolactin for 48 hours of hormone treatment.

In summary, the treatment with wild-type human prolactin for 48 hours retained a normal cellular morphology and viability. In contrast, the treatment with Δ41–52 human prolactin produced morphology consistent with cell death (detachment, loss of cell-cell contact, nuclear fragmentation). These experiments for the first time show that Δ41–52 human prolactin, an antagonist of the induced-fit type, can kill human breast cancer cells. The fragmentation of the nucleus suggests that T47D cells are undergoing programmed cell death also known as apoptosis.

Example 9

Changes in Gene Expression by Δ41–52 Human Prolactin

Gene chip technology was used to assess the effects of treating T47D human breast cancer cells with Δ41–52 human prolactin. Gene chip studies allow the investigator to simultaneously monitor changes in the expression of approximately 30,000 genes. Such an approach allows the identification of changes in complex processes, such as apoptosis.

T47D human breast cancer cells were grown in media to approximately 75–80% confluence. Prior to the start of the experiment, the cells were washed twice in media without phenol red and placed in starvation media (1% charcoal-stripped fetal bovine serum). After 24 hours of starvation, the media was replenished with the following:

Control: 1% charcoal-stripped fetal bovine serum containing media;

Wild-type human prolactin: 1% charcoal-stripped fetal bovine serum containing media with 0.3 nM recombinant human prolactin; and Δ41–52 human prolactin: 1% charcoal-stripped fetal bovine serum containing media with 500 nM Δ41–52 human prolactin.

Cells were exposed to the above hormone concentrations for 48 hours. Total RNA from each culture flask was isolated using Qiagen's RNEASY™ kit, which uses techniques common to the art. The quality and concentration of the total RNA was determined by formaldehyde agarose gel electrophoresis and spectroscopy, respectively.

Total RNA from each treatment group was submitted to The Ohio State University Comprehensive Cancer Center Microarray Facility for cRNA preparation and microarray analysis. Affymetrix U133 human gene chip set (U133A&B) was used for microarray analysis. Probe-set annotations were based on the latest available Human UniGene Version Number (hs. 154). The results from the control experiment (no hormone treatment) were subtracted from both hormone-treated groups (wild-type or Δ41–52 human prolactins). The results from the two hormone-treatment groups were then compared. For statistical analysis, p-values were derived from a two-way ANOVA test for significant effects. Scaled differential expression estimates were made after applying a Bonferroni correction.

The results showed that there was statistically significant Δ41–52 human prolactin-dependent up-regulated expression of 47 genes and Δ41–52 human prolactin-dependent down-regulated expression of 22 genes. Identification of some of these genes is shown in the Tables 3, 4 and 5.

The largest group of statistically significant Δ41–52 human prolactin-dependent up-regulated gene expression involved genes whose expression is associated with apoptosis and regulation of cell cycle/cell cycle arrest.

TABLE 3

Apoptosis, cell cycle control and tumor-suppressor related genes up regulated by Δ41-52 human prolactin.

| Gene abbreviation | gene name |
|---|---|
| | Genes Promoting Apoptosis |
| NFK-BIA | nuclear factor-kB inhibitor A |
| BOK | BCL-2 related ovarian killer |
| DFFB | 40 kDa subunit of DNA fragmentation factor |
| CEBPd | CCAAT/element binding protein δ |
| TNFSF14 | Ligand for Apo-3 receptor |
| DAXX | FAS binding protein |
| | Genes Inhibiting Apoptosis |
| BIRC5 | survivin |
| Api-5 | apoptosis inhibitor 5 |
| AVEN | caspase activation inhibitor |

These data positively correlate with Western blots showing increased expression of apoptosis related proteins including Caspase 3 and Caspase 7 in Δ41–52 human prolactin-treated T47D human breast cancer cells.

Other pathways up-regulated by the Δ41–52 human prolactin relate to cell surface markers, cell-cell signaling, intercellular junctions, extracellular matrix, ion transport and calcium binding, complement activation, and regulation of RNA polymerase 11 transcription (Table 4).

TABLE 4

| Additional genes up regulated by Δ41-52 human prolactin. | |
|---|---|
| C3 | complement component 3; plasma glycoprotein; classical complement activation cascade; G protein linked receptor protein signaling |
| BF | B-factor, properdin; alternative complement pathway C3/C5 convertase; MHC complex antigen; serine-type peptidase |
| SLC12A3 | solute carrier family 12 member 3; sodium:chloride symporter |
| STEAP | six transmembrane epithelial antigen of the prostate; channel pore transporter; integral plasma membrane protein; intercellular junctions |
| ECGF | endothelial cell growth factor 1, platelet derived; cell-cell signaling |
| PLAB | prostate differentiation factor; cell-cell signaling; signal transduction; (TGFB receptor signaling pathway) |
| CTGF | connective tissue growth factor, cell migration/motility, extracellular matrix; basement membrane |
| COL12A1 | collagen type XII alpha 1; extracellular membrane structural protein conferring tensile strength |
| CYP7A1 | cytochrome P450; cholesterol 7-alpha-monooxygenase; steroid hydroxylase |
| C8FW | phosphoprotein regulated by mitogenic pathways; protein kinase |
| S100A8 | calgranulin A; calcium binding |
| EEF2 | eukaryotic translation elongation factor 2; GTP binding |
| GPRC5B | G protein-coupled receptor |
| PLA2G4C | phospholipase A2, calcium-independent; phospholipid metabolism |
| ZNF42 | zinc finger protein 42, retinoic acid responsive, POL II transcriptional regulation |
| MAFF | musculoaponeurotic fibrosarcoma oncogene homolog, POL II transcription; DNA-binding |

The most significant gene expression down-regulated by A41–52 human prolactin, other than anti-apoptosis genes, involve G-protein-coupled receptors, cellular enzymes, inhibitors (kinase, metalloprotease) and cell migration/vesicle transport related pathways (Table 5).

TABLE 5

| Genes down regulated by Δ41-52 human prolactin. | |
|---|---|
| OPHN1 | oligophrenin 1; substrate-bound cell migration; RHO GTPase activator |
| GPR35 | G protein-coupled receptor; signal transduction |
| GFMB | glial maturation factor beta; protein kinase inhibitor |
| RECK | reverse inducing cysteine rich protein with kazal motifs; metalloprotease inhibitor |
| PKM2 | pyruvate kinase; glycolysis; catabolic carbohydrate metabolism |
| RAB6K1FL | RAB 6 interacting, kinesin-like; vesicle transport, microtubules, Golgi apparatus |
| HPRT1 | hypoxanthine phosphoribosyltransferase 1; purine salvage; nucleoside metabolism |
| AD24 | aspartate β hydroxylase |
| FLJ21032 | fatty acid desaturase |

The up-regulation of a significant number of genes associated with apoptosis shows that Δ41–52 human prolactin is inducing cell death by antagonizing the prolactin autocrine system in the T47D human breast cancer cells. The induction of programmed cell death (apoptosis) supports the morphologic observations where treatment of T47D human breast cancer cells with Δ41–52 human prolactin induced a morphologically consistent with apoptosis and cell death. With these data, we show the efficacy of Δ41–52 human prolactin as an antagonist of human prolactin and a potential treatment for human breast cancer.

Example 10

Δ41–52 Human Prolactin Kills Jurkat Cells in a Dose and Time-dependent Fashion

Human prolactin has long been thought to control the growth and differentiation of human T-cell, a subgroup of cells that belong to the immune system. Jurkat cells are a line of cells derived from cells from a human T-cell leukemia. These cells have been grown in culture for many years and are well characterized. Recently, Jurkat cells have been reported to express both prolactin and the prolactin receptor (Matera, L., Cutufia, M., Geuna, M., Contarini, M., Buttiglieri, S., Galin, S., Fazzari, A. and Cavalieri, C., *Journal of Neuroimmunoloqy* 79:12–21 (1997)). Since prolactin is most often thought of as a hormone that promotes proliferation or differentiation of target cells, we did not necessarily expect T47D human breast tumor cells to respond to Δ41–52 human prolactin by promoting both the morphology and gene expression patterns associated with apoptosis. We therefore sought an unrelated tumor cell line where we could determine if Δ41–52 human prolactin would also induce apoptosis. We chose a T-cell derived cell line because it has the components required for a prolactin autocrine system and because these cells do not adhere to the surface of their culture flask. This latter property allows us to use flow cytometry as a tool to evaluate the effects of treatments on individual cells in many treatment variables including time of treatment, dose of hormone, and type of prolactin.

We chose to treat actively growing cultures of Jurkat cells with no treatment, wild-type human prolactin, Δ41–52 human prolactin, or G129R human prolactin at doses from the sub-nanomolar range to the micromolar range, and for various times up to 96 hours. At the end of the treatment period the cells were mixed with two fluorescent stains. The first measures the potential across the mitochondrial membrane (3,3' dihexyloxacarbocyanine iodide, DiOC) and a second fluorescent dye (propidium iodide, PI) that is able to enter dead cells and intercalate with the DNA and provide a fluorescent signal, but is kept out of living cells. The cells are then enumerated by a flow cytometer that measures the fluorescence signals from both fluorescent dyes for each cell (approximately 10,000 cells were measured for each treatment). In addition, controls were performed with agents that would provide both positive and negative controls for apoptosis. If treatment by agents induces apoptosis, then effected cells will first loose their mitochondrial membrane potential (an early event during apoptosis) and then increase the PI fluorescence signal as the cells die.

The results for each test can be displayed on an X/Y axis with the fluorescence intensity of each dye displayed by a log scale (FIG. 16). The measurements for individual cells are displayed as points indicating both their PI and DiOC signals. Normal untreated cells have high DiOC signals and low PI signals, they can be observed on the lower right portion of the figure. As cells begin apoptosis, the DiOC signal will first diminish as apoptosis begins (lower left portion of the figure) and then the PI signal will increase as cells finally die and loose their ability to exclude PI (upper left portion of the figure).

Cells in each portion of the figure can be counted and the percentages of cells in each condition can be calculated and related to treatment (FIGS. 17 and 18). Jurkat cells are put into apoptosis by treatment with Δ41–52 human prolactin. The dose response curve shows that the optimal dose over the times tested is 1 nM and that by 96 hours the viable Jurkat cells have dropped from approximately 95% to between 25 and 30%. During the time of treatment the proportion of cells in apoptosis is increased suggesting that treatment kills the cells by inducing apoptosis. Thus, cells derived from a human T-cell leukemia are dependent on human prolactin for viability, and may be killed by treatment with a potent human prolactin antagonist. Further Jurkat cells treated with either wild-type human prolactin or the weaker G129R human prolactin antagonist do not respond to these treatments by decreased cellular viability. These results are a specific example where our new class of prolactin antagonists (exemplified by Δ41–52 human prolactin) clearly out perform the best characterized prolactin antagonist of the class that attempts to eliminate agonist activity by steric blockage of site 1.

Except where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The specification is most thoroughly understood in light of the teachings of the references cited within the specification, all of which are hereby incorporated by reference in their entirety. The embodiments within the specification provide an illustration of embodiments of the invention and should not be construed to limit the scope of the invention. The skilled artisan recognizes that many other embodiments are encompassed by the claimed invention and that it is intended that the specification and examples be considered as exemplary only, with a true scope and spirit of the invention being indicated by the following claims.

What is claimed is:

1. A modified human prolactin molecule that exhibits the following characteristics:

1) exhibits antagonist activity;

2) binds to prolactin receptor through site 1;

3) does not bind to prolactin receptor through site 2 or has diminished binding through site 2; and 4) exhibits less than 1% of unmodified prolactin's agonist activity;

wherein the prolactin molecule comprises at least one mutation in a region selected from i) amino acids 41–57, ii) amino acids 94–110, and iii) amino acids 160–173; and wherein the at least one mutation is selected from deletions, replacements, and insertions.

2. The modified human prolactin molecule according to claim 1, wherein the prolactin molecule exhibits less than 0.9% of unmodified prolactin's agonist activity.

3. The modified human prolactin molecule according to claim 2, wherein the prolactin molecule exhibits less than 0.5% of unmodified prolactin's agonist activity.

* * * * *